(12) United States Patent
Swerdlow et al.

(10) Patent No.: US 6,675,042 B2
(45) Date of Patent: Jan. 6, 2004

(54) DEFIBRILLATION SHOCK STRENGTH DETERMINATION TECHNOLOGY

(76) Inventors: Charles D. Swerdlow, 457 Kenter Ave., Los Angeles, CA (US) 90049; Kalyanam Shivkumar, 919 Levering Ave., Los Angeles, CA (US) 90024

( * ) Notice: Subject to any disclaimer, the term of this patent is extended or adjusted under 35 U.S.C. 154(b) by 0 days.

(21) Appl. No.: 10/351,143

(22) Filed: Jan. 27, 2003

(65) Prior Publication Data

US 2003/0195569 A1 Oct. 16, 2003

Related U.S. Application Data

(60) Provisional application No. 60/372,402, filed on Apr. 15, 2002.

(51) Int. Cl.$^7$ ................................................ A61N 1/39
(52) U.S. Cl. ............................................................ 607/8
(58) Field of Search ................................ 607/1, 2, 5–8, 607/68–72

(56) References Cited

U.S. PATENT DOCUMENTS

| | | | | |
|---|---|---|---|---|
| 5,105,809 A | * | 4/1992 | Bach et al. | 607/5 |
| 5,129,392 A | * | 7/1992 | Bardy et al. | 607/2 |
| 6,052,621 A | * | 4/2000 | Begemann et al. | 607/2 |

* cited by examiner

*Primary Examiner*—George R. Evanisko
(74) *Attorney, Agent, or Firm*—Skinner & Associates

(57) ABSTRACT

A method for determining a cardiac shock strength, for example the programmed first-therapeutic shock strength of an implantable cardioverter defibrillator (ICD), including the steps of sensing a change in a T-wave of an electrogram with respect to time such as the maximum of the first derivative of a T-wave of an electrogram; delivering a test shock by (i) delivering a test shock at a test-shock strength and at a test-shock time relating to the maximum of the first derivative of the T-wave with respect to time; and (ii) sensing for cardiac fibrillation. If fibrillation is not sensed, test-shock delivery is repeated at the same test-shock strength and at specific, different test-shock times relating to the maximum of the first derivative of the T-wave. If fibrillation is still not sensed, the shock strength is decreased and test shocks are repeated at the same specific test shock times relative to the maximum of the first derivative of the T-wave. And if fibrillation is sensed, the programmed therapeutic shock strength of the ICD is set as a function of the incrementally greater test-shock strength. Also disclosed is an apparatus for selecting a programmed first-shock strength of an ICD, including a shock subsystem for delivering therapeutic shocks and test shocks to the heart, and a ULV subsystem connected to the shock subsystem, to provide test shocks of test-shock strengths and at test-shock times relating to the maximum of the first derivative of the T-wave with respect to time, and to determine the therapeutic shock strength of the ICD as a function of the test-shock strengths.

112 Claims, 7 Drawing Sheets

Figure 3
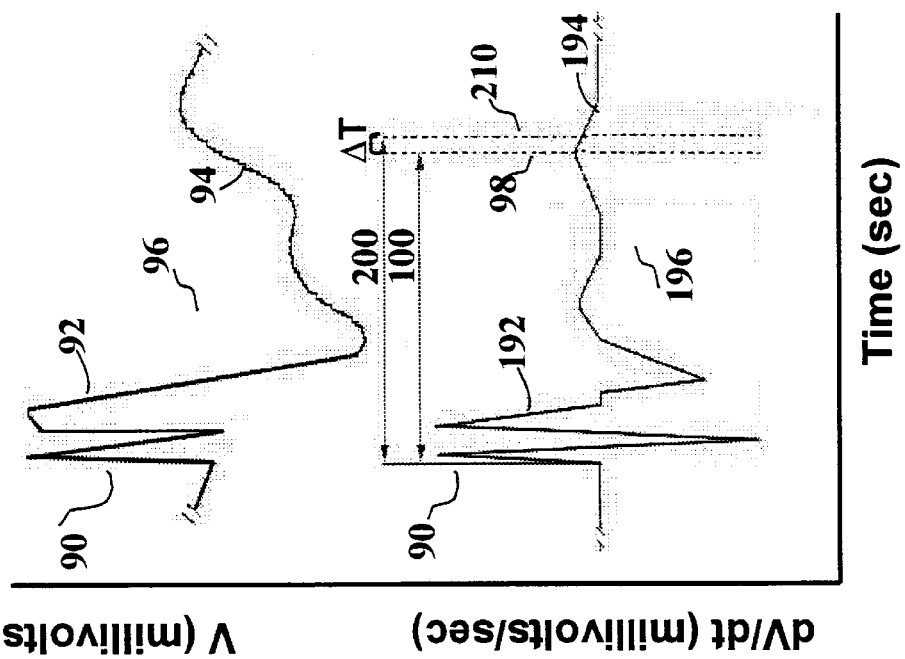
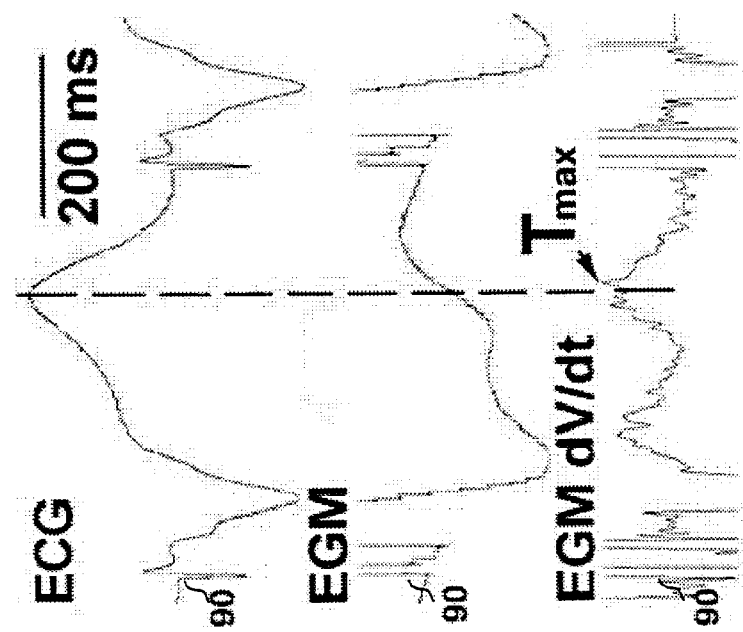

Figure 6: Timing Difference: Peak of Latest-Peaking T-Wave on Surface ECG vs. Maximum Derivative of T-Wave from ICD Electrodes

DEFIBRILLATION SHOCK STRENGTH DETERMINATION TECHNOLOGY

CROSS-REFERENCE TO RELATED APPLICATIONS, IF ANY

This application claims the benefit under 35 U.S.C. §119 (e) of U.S. Provisional Patent Application Ser. No. 60/372,402, filed Apr. 15, 2002, which is hereby incorporated by reference.

STATEMENT REGARDING FEDERALLY SPONSORED RESEARCH OR DEVELOPMENT

Not applicable.

REFERENCE TO A MICROFICHE APPENDIX IF ANY

Not applicable.

BACKGROUND OF THE INVENTION

1. Field of the Invention

The present invention relates, generally, to implantable cardioverter defibrillators (ICDs) and defibrillation methods, and particularly to a method and apparatus for determining the optimal shock strength for defibrillation, and most particularly to determining the upper limit of vulnerability (ULV) based on changes with respect to time in the T-wave of the cardiac signal, preferably the maximum of the first derivative of the T-wave with respect to time measured preferably exclusively from implanted electrodes. Unless otherwise indicated, the term "derivative of the T-wave" refers to the first derivative of the T-wave with respect to time. The technology is useful for automating the process of selecting the first defibrillation shock strength for ICDs.

2. Background Information

Heart disease is a leading cause of death in the United States. The most common form of cardiac death is sudden, caused by cardiac rhythm disturbances (arrhythmias) in the form of a ventricular tachycardia or ventricular fibrillation.

Ventricular tachycardia is an organized arrhythmia originating in the ventricles. It results in cardiac contractions that are too fast or too weak to pump blood effectively. Ventricular fibrillation is a chaotic rhythm disturbance originating in the ventricles that causes uncoordinated cardiac contractions that are incapable of pumping any blood. In both ventricular tachycardia and ventricular fibrillation, the victim will most likely die of "sudden cardiac death" if the normal cardiac rhythm is not reestablished within a few minutes.

Implantable cardioverter defibrillators (ICDs) were developed to prevent sudden cardiac death in high risk patients. In general, an ICD system consists of implanted electrodes and a pulse generator that houses implanted electrical components. The ICD uses implanted electrodes to sense cardiac electrical signals, determine the cardiac rhythm from these sensed signals, and deliver an electrical shock to the heart if life-threatening ventricular tachycardia or ventricular fibrillation is present. This shock must be of sufficient strength to defibrillate the heart by simultaneously depolarizing all or nearly all heart tissue.

Shock strength is typically measured as shock energy in Joules (J). The defibrillating shock interrupts the abnormal electrical circuits of ventricular tachycardia or ventricular fibrillation, thereby permitting the patient's underlying normal rhythm to be reestablished. ICD pulse generators are implanted within the patient and connected to the heart through electrodes to provide continuous monitoring and immediate shocking when a life-threatening rhythm disturbance is detected. Because the devices must be small enough for convenient implantation, ICDs are limited in their ability to store electrical energy. In general, ventricular tachycardia can be terminated by weaker shocks than those required to terminate ventricular fibrillation. Thus ICDs must deliver a sufficiently strong shock to insure reliable defibrillation in response to each occurrence of ventricular fibrillation.

One method is to use the maximum shock strength of the ICD for each shock. However, this approach is an inefficient use of the ICD's limited stored electrical energy and will unnecessarily reduce the useful life of an ICD pulse generator.

It is well known in the art that the shock strength required to defibrillate a human heart effectively varies with the implanted lead configuration and placement as well as the individual heart's responsiveness to the shock. To maximize efficiency of an ICD system, the minimum shock strength necessary to defibrillate an individual patient's heart reliably must be determined.

However, it is also well known in the art that the relationship between an ICD's defibrillation shock strength and success or failure of defibrillation is represented by a probability-of-success curve rather than an all-or-none defibrillation threshold (DFT). Very weak, low strength (low energy) shocks never defibrillate. Very strong shocks, at energies greater than the maximum output of ICDs, always defibrillate. However, clinically relevant shock strengths for ICDs lie between these two extremes. In this intermediate range of shock strengths, a shock of a given strength may defibrillate successfully on one attempt and not on another attempt.

Determining a complete curve of the probability of success for every possible shock strength requires many fibrillation-defibrillation episodes. In clinical (human) studies and procedures, the number of fibrillation-defibrillation episodes should be limited because of their associated risks. Thus the goal of testing at the time of ICD implant cannot be to determine a complete probability of success curve. In general, the goal of testing at ICD implant is to provide an accurate estimate of the minimum shock strength that defibrillates with a high probability of success while using a minimum amount of testing. The shock energy that defibrillates with an X% probability of success is referred to as the defibrillation threshold$_x$ or DFT$_X$. Thus a goal of clinical testing at ICD implantation is to estimate a shock strength in the range of the DFT$_{95}$–DFT$_{99}$. This is the optimal strength at which to program the first shock of an ICD. For research purposes, it may be preferable to estimate the DFT$_{50}$.

The minimum measured shock strength that defibrillates during a given session of defibrillation testing is referred to, in general, by the term DFT, despite the fact that no true threshold for defibrillation exists. All methods for determining the DFT of an ICD system require inducing fibrillation a number of times and testing various shock strengths for defibrillation through the implanted defibrillation leads. In the commonly used step-down method defibrillation is attempted at a high shock strength that is likely to defibrillate the heart successfully. If this shock is unsuccessful, a stronger "rescue shock" is delivered to effect defibrillation. Regardless of the outcome of the defibrillation shock, there is a waiting period of about 5 minutes to permit the patient's heart to recover. If the defibrillation shock is successful, fibrillation is reinitiated and the defibrillation is attempted at a lower shock strength. This process is repeated with successively lower defibrillation shock energies until the shock does not defibrillate the heart. The minimum shock strength that defibrillates is the DFT. Depending on the initial shock strength, the DFT determined in this manner is usually between the $DFT_{30}$ and $DFT_{70}$. The ICD is then programmed to a first-shock strength selected to be an estimate of the lowest value that can reliably achieve defibrillation by adding an empirically-determined safety margin to the DFT.

Other methods for determining the DFT require additional fibrillation-defibrillation episodes after a defibrillation shock has failed. In these methods, fibrillation is reinitiated after a failed defibrillation shock and defibrillation is attempted at successively higher shock strengths until a shock defibrillates the heart successfully. This change from a shock strength that does not defibrillate to one that does (or vice versa) is called a reversal of response. DFT methods may require a fixed number of reversals. If the size of the shock increments and decrements is the same, a multiple-reversal (up-down) method provides a good estimate of the $DFT_{50}$. An alternative Bayesian method uses a predetermined number of unequal shock increment steps and decrement steps to estimate an arbitrary, specific point on the DFT probability of success curve.

One significant disadvantage of all DFT methods is the necessity to repeatedly fibrillate and then defibrillate the patient's heart to determine the DFT. For example, U.S. Pat. No. 5,531,770 describes a method of DFT testing that is described as an advantage because it limits the number of fibrillation-defibrillation episodes to 5, in contrast to other methods such as the "three-reversal" method that may require more episodes. These repeated episodes of fibrillation and defibrillation may have an adverse effect on the patient. Further, each fibrillation episode is associated with a small risk that the patient cannot be defibrillated and will thus die. Considerable time must be spent between test cycles in order to provide the patient's heart time to recover from the previous round of fibrillation-defibrillation.

A second disadvantage is that successful defibrillation is a probability function of shock energy, not an all or none phenomenon described by a simple threshold. Since the usual clinical DFT method results in a measurement somewhere in the broad range between the $DFT_{30}$ and $DFT_{70}$, optimal ICD programming cannot be achieved by adding a single empirically-determined shock increment. The resulting programmed first shock strength sometimes results in selecting a shock that either does not defibrillate reliably or unnecessarily uses excessive energy.

It is known in the art that shocks delivered during the vulnerable period of the normal cardiac cycle induce ventricular fibrillation, providing that the shock energy is greater than a minimum value and less than a maximum value. The ULV is the shock strength at or above which fibrillation is not induced when a shock is delivered during the vulnerable period of the normal cardiac cycle. The ULV may be displayed graphically as the peak of the vulnerable zone, a bounded region in a two-dimensional space defined by coupling interval (time) on the abscissa and shock strength on the ordinate. The ULV, which can be measured in regular rhythm, corresponds to a shock strength that defibrillates with a high probability of success and correlates strongly with the DFT. Because the ULV can be determined with a single fibrillation-defibrillation episode, it has the potential to provide a patient-specific measure of defibrillation efficacy that requires fewer fibrillation-defibrillation episodes than DFT testing.

Although the vulnerable period occurs generally during the T-wave of the surface electrocardiogram (ECG), its precise timing varies from individual to individual. More importantly, the peak of the vulnerable zone, which corresponds to the most vulnerable time intervals in the cardiac cycle, also varies from individual to individual. Accurate determination of the ULV depends critically delivering a T-wave shock at the peak of the vulnerable zone.

Several methods of determining the defibrillation shock strength for ICDs are based on the ULV. One such method is disclosed in U.S. Pat. No. 5,105,809. This method begins by applying an initial electrical shock to the patient's heart during the vulnerable period. The shock is timed during the "occurrence of the T-wave." The shock strength of the initial shock is sufficiently high so as to have a low probability of initiating fibrillation. Assuming this initial shock fails to induce fibrillation, a second shock of less magnitude is delivered with the same timing during a subsequent vulnerability period. The process is repeated with successive shocks of lesser magnitudes until fibrillation is induced. When fibrillation finally occurs, the energy of the preceding shock that did not cause fibrillation is the shock strength required to defibrillate. This method does not disclose how the single shock at each energy is timed to coincide with the peak of the vulnerable zone. Indeed, it does not mention the peak or most vulnerable time in the vulnerable zone.

Another method for establishing a ULV is disclosed in U.S. Pat. No. 5,346,506. The method relies on research demonstrating that the 50% probability of successful defibrillation can be approximated by determining the 50% probability that a shock exceeds the ULV. A shock is applied to the heart through epicardial patches at a predetermined limited period of time centered on the mid-upslope of the T-wave. The disclosure argues that the total number of shocks is reduced by not having to scan the entire T-wave with shocks. A disadvantage of this method is that the shock strength for the first application must be estimated beforehand. The number of shocks required to determine the DFT is reduced only if the estimated 50% probability of reaching the ULV is quite accurate. Further, this method requires multiple fibrillation-defibrillation episodes, with their attendant risks, to provide an accurate estimate of the shock energy required to achieve a 50% probability of successful defibrillation.

U.S. Pat. No. 5,954,753 discloses that the ULV can be determined by one or two T-wave shocks timed near the peak of the T-wave, preferably about 10% of the QT interval or 30 ms before the peak.

The methods described in U.S. Pat. No 5,105,809, U.S. Pat. No. 5,346,506, and U.S. Pat. No. 5,954,753 depend critically on accurate, a priori knowledge of the timing of the peak of the vulnerable zone because shocks are delivered at only one or two time intervals. Because the timing of this peak differs relative to any fixed point in the T-wave from patient to patient, it is not necessarily contemporaneous with any single timing interval based on the T-wave. As a result, these methods are susceptible to error because the specific time during the T-wave at which shocks are delivered may have substantially less vulnerability than peak of the vulnerable zone. If T-wave shocks are not delivered at the peak of the vulnerable zone, the ULV will be underestimated. This discrepancy will not be appreciated at the time of implantation and therefore these methods may substantially underestimate the required defibrillation shock energy setting.

Further, as will be seen in the discussion of U.S. Pat. No. 5,564,422 below, U.S. Pat. No. 5,954,753 does not identify the peak of the vulnerable zone relative to the peak of the T-wave since the interval it teaches for timing of T-wave shocks is shorter than the most vulnerable intervals for typical clinically-used transvenous ICD systems.

U.S. Pat. No. 5,564,422 to Chen and Swerdlow, which is incorporated by reference, usually provides a reliable estimate of the DFT for the clinical purpose of implanting an ICD for two-electrode transvenous defibrillation systems. However, such systems are no longer in widespread use. However, in practice, the method and apparatus disclosed in this patent has been found to require measuring and analyzing multiple surface ECG leads. The method and apparatus disclosed in this patent cannot be performed using intra-cardiac leads exclusively.

The Chen and Swerdlow method bases the timing of T-wave shocks on the latest-peaking monophasic T-wave recorded from the surface ECG. The timing of the peak of the T-wave varies substantially among ECG leads as a consequence of QT-interval dispersion. In different patients, the latest-peaking monophasic T-wave occurs unpredictably in various surface ECG leads. Even a small error in measuring the pacer spike to peak interval of the latest-peaking monophasic T-wave can result in errors in the measured ULV and thus compromise its value as a clinical tool. Thus, to be used accurately, this method requires measurement and analysis of intervals from multiple (preferably all 12) standard surface ECG leads to identify the lead with the latest-peaking monophasic T-wave.

The Chen and Swerdlow method cannot be performed using ECGs recorded exclusively from implanted electrodes (electrograms). Implanted electrodes, particularly those including intra-cardiac electrodes, often have biphasic rather than monophasic T-waves as shown in FIG. 3. When this occurs, the peak of the (monophasic) T-wave is undefined and this method cannot be applied. Further, even if an intra-cardiac electrode has a monophasic T-wave, the peak may precede that of a surface ECG lead.

This limitation also applies to the method of U.S. Pat. No. 5,954,753 which depends on identification of the peak of the T-wave. This method recommends identification of the peak of T-waves recorded from ICD electrograms, which usually have biphasic T-waves. FIG. 3A shows that the peak of the latest-peaking monophasic T-wave on the surface ECG agrees closely with the peak of the derivative of the intra-cardiac electrogram, but not with the peak of the biphasic intracardiac electrogram. Further, as FIG. 3A shows, the T-wave recorded from an intracardiac electrogram often is low in amplitude. Thus identification of its peak may be subject to significant measurement error.

The present invention differs from the Chen and Swerdlow (U.S. Pat. No. 5,564, 422) method in several respects, including but not limited to, that the coupling interval of T-wave shocks is based on the point of maximum derivative of the repolarization phase (T-wave) of an electrogram recorded from an implanted electrode, whether the T-wave is biphasic or monophasic. This approach involves the concept of the activation-recovery interval. The activation-recovery interval is the interval between the times of minimum derivative of the ventricular electrogram and maximum derivative of the T-wave in a unipolar intra-cardiac electrogram. Theoretical analysis predicts that maximum derivative of the T-wave is proportional to a spatial weighting function of the third temporal derivative of the cardiac action potential. Because the maximum of the first temporal derivative of the action potential times very closely with the maximum of its third temporal derivative, the activation-recovery interval has been used as a measure of local repolarization in basic physiologic studies. Because the activation-recovery interval acts as a spatial average, it is dominated by the action potentials of cells closest to the recording site. The activation-recovery interval recorded from a point, intra-cardiac electrode has been used to assess local repolarization. For example, it has been used to assess dispersion of local repolarization intervals in canines and local effects of catheter ablation in humans.

In an embodiment of the present invention, the analyzed electrogram may be recorded from large extra-cardiac or intra-cardiac electrodes. Recordings from these large electrodes contain more information regarding global repolarization than recordings from point electrodes.

An additional limitation of the method of Chen and Swerdlow (U.S. Pat No. 5,564,422) is that the timing of the latest peaking T-wave is measured only once at the beginning of testing. Research has shown that the interval between the pacer spike and the peak of the latest peaking T-wave may change over time during the testing procedure as a result of shock delivery. Since the method of Chen and Swerdlow (U.S. Pat. No. 5,564,422) sets the timing of all subsequent shocks by using the initial measurement of the interval between the pacer spike and peak of the latest-peaking monophasic T-wave, subsequent shocks may not be delivered at the desired time relative to the peak of the latest peaking T-wave at the moment the shock is delivered. Even a small error in measuring the pacer spike to peak interval of the latest-peaking monophasic T-wave (of the order introduced by post-shock changes that occur during clinical testing after several shocks) can result in errors in the measured ULV and thus compromise its value as a clinical tool. (Swerdlow C D, Martin D J, Kass R M, Davie S, Mandel W J, Gang E S, Chen P S. The zone of vulnerability to T-wave shocks in humans. *J Cardiovasc Electrophysiol.* 1997;8:145–54.) An embodiment of the method of the present invention avoids such errors by re-measuring the pacer spike to peak interval of the derivative of the intra-cardiac T-wave automatically after each shock.

A further limitation of the method of Chen and Swerdlow (U.S. Pat. No. 5,564,422) is that it does not scan the vulnerable zone completely for the defibrillation electrode configuration most commonly used in clinical practice today. This may lead to underestimation of the ULV in some patients, which in turn may lead to programming of insufficient first ICD shock strengths and failed defibrillations. The method of Chen and Swerdlow usually provides an adequate scan of the vulnerable zone when shocks are delivered using a two-electrode system from right-ventricular coil to left-pectoral ICD case (also referred to as the "housing" or "can"). (Swerdlow C D, Martin D J, Kass R M, Davie S, Mandel W J, Gang E S, and Chen P S, in The Zone of Vulnerability to T-wave shocks in Humans, *J Cardiovasc Electrophysiol.* 1997; 8: 145–54). However, in present ICDs, the principal shock pathway uses a different three-electrode system to deliver shocks from right-ventricular coil to left-pectoral case plus a superior vena cava electrode. It provides superior defibrillation to the two-electrode system. Recently the inventor has demonstrated that the peak of the vulnerable zone using this three-electrode defibrillation configuration may not be at any of the intervals tested in the method of Chen and Swerdlow (U.S. Pat. No. 5,564,422) or those tested in the method of U.S. Pat. No. 5,954,753. Instead the most vulnerable intervals time after the peak of the latest peaking T-wave in some patients. In fact, in 5 of 25 patients tested (20%), the peak of the vulnerable zone occurred at least 20 ms beyond the peak of the latest peaking T-wave. In these patients, the methods of U.S. Pat. No. 5,564,422 and U.S. Pat. No. 5,954,753 do not accurately identified the ULV.

In one embodiment of the present invention, four shocks are used to scan the vulnerable zone reliably in humans. When the surface ECG is used as a reference, these shocks should be delivered at −40 ms, −20 ms, 0 ms, and +20 ms relative to the peak of the latest-peaking monophasic T-wave. Clinical application of this four-shock method with T-wave shocks timed relative to the surface ECG has resulted in programming of shock strengths that defibrillate with near uniform success for both two-electrode and three-electrode defibrillation configurations. Research has demonstrated that the shock strength equal to the step-down ULV determined by the present invention, successfully defibrillates 90% of the time with a 95% confidence level of plus or minus 8%. When the shock strength is increased to a value that is 3 Joules above the measured ULV, the rate of successful defibrillation is 100% with a confidence level greater than 95%.

For the present, standard three-electrode right-ventricular coil to left-pectoral case plus a superior vena cava shock pathway, three shocks at −20 ms, 0 ms, and +20 ms relative to the peak of the latest-peaking monophasic T-wave correctly identified the most vulnerable intervals in all 25 of 25 patients tested (100%). In the same patients, if shocks were timed relative to the maximum of the derivative of the T-wave, four shocks timed at −20 ms, 0 ms, and +20 ms, and +40 ms were required to identify the most vulnerable intervals in 24 of 25 patients (96%). In the remaining patient, the T-wave scan missed the most vulnerable interval by 9 ms. Thus, for the three-electrode shock pathway an alternative embodiment delivers up to three test shocks at −20 ms, 0 ms, and +20 ms relative to the peak of the latest-peaking monophasic surface T-wave. A second alternative embodiment for this three-electrode shock pathways delivers up to four test shocks at −20 ms, 0 ms, and +20 ms, and +40 ms relative to the maximum of the derivative of the T-wave of the ICD electrogram.

All US patents and patent applications, and all other published documents mentioned anywhere in this application are incorporated by reference in their entirety.

BRIEF SUMMARY OF THE INVENTION

The present invention provides an automatic ICD system and method which is practical, reliable, accurate, and efficient, and which is believed to fulfill the need and to constitute an improvement over the background technology. The system and method quickly and accurately determines the optimal first shock strength of an ICD system for a patient by evaluating the heart's ULV during or after implantation. As noted above, the ULV, if measured correctly, correlates closely with a shock strength that defibrillates with a high probability of success.

The system and method of the present invention involve delivering one or a series of shocks to the heart in paced or native rhythm. The shocks are timed in relation to a change with respect to time in the T-wave of a cardiac signal. Preferably, the signal is an electrogram recorded from totally-implanted electrodes. Preferably the change with respect to time is the first, ordinary derivative with respect to time of the T-wave.

Methods and rationale for the determination and manipulation of ordinary derivatives of single or multi-dimensional functions to understand the complexities of change or variation as it occurs across the range of one or more independent variables are well-known in the art. The ordinary derivative for a single function is well-known to represent local changes or variations, and there exists many methods to determine the position of these local changes with respect to a set of values for an independent variable.

For example, as it relates to the present invention, a single dimensional function comprises electrogram or ECG data sampled from a patient over a period of time that represents the patient's cardiac cycle. The derivative of this function with respect to time over the course of a predetermined single cardiac cycle is a function that represents a set of local changes or variations that occurred in the electrogram or ECG function during that time period. A second derivative function of this derivative function further determines local changes in the first derivative across the time period, and represents additional information regarding changes in the electrogram or ECG function.

Iterating the process of derivatives of derivatives captures the totality of information in a function regarding the changes or variations that occurs in the function over the range of an independent variable. Functions that are constructed using the iterative process are called second ($2^{nd}$) derivatives, third ($3^{rd}$) derivatives, fourth ($4^{th}$) derivatives, no derivatives, and so on. These methods can be applied to multi-dimensional functions and these methods are further developed to provide partial derivatives, which determine local changes in a multi-dimensional function as these changes related to a subset of the independent variables.

There are well-known methods that further differentiate these local changes or variations into various types or kinds of changes. For example, a local change in a function may indicate whether the function has a local minimum, local maximum, or local saddle point at a value of an independent variable. A local minimum and a local maximum are called extreme points for the function. For example, a local maximum of an ECG function during a T-wave indicates a point at which cardiac-related repolarization changes cause the largest change in a patient's iso-electric potential as it is measured using an ECG device.

Furthermore, a local maximum and a local minimum of a derivative of an ECG function during a T-wave can indicate points at which the local changes during the cardiac-related repolarization are changing or varying at the highest rates.

Furthermore, there are well methods for easily determining these local changes or variations in a function or one of its derivatives. For example, a local maximum for a function is a value of the function at a point A such that $f(A) \geq f(x)$ for all other values x of the independent variable near the value A. A local minimum for a function is a value of the function at a point A such that $f(A) \leq f(x)$ for all other values x of the independent variable near the value A. The set of local maximums and minimums are quickly determined by taking the derivative of the function, determining the independent variable values for which the function's derivative is zero (called critical numbers), and applying the test described above to each of these values.

There are many different types of derivatives (or differentials) as well that may be applied to a function to determine information regarding a local change in the function, depending on the dimensionality and complexity of the function. An important subset of these different types of derivatives comprises a directional derivative, a partial derivative, an implicit differential, a variance calculation, a bounded variation calculation, a tangent vector approximation, and the first order differential operators from vector calculus such as div, grad, and curl.

The theory and application of derivatives are most applicable to functions that are modeled as continuous functions. Functions used by methods and apparatus that construct these functions from sampled data as a part of the invention operation are discrete functions that are appropriately modeled by continuous functions, and it is well-known that the methods for continuous functions can be applied to them. Such functions are called discrete analogs for continuous functions, and as such all the derivative and differential methods have appropriate discrete analogs that are applied to these functions to determine the totality of information as the information is reflected by changes in the functions previously described.

For example, an important discrete analog methodology that is well-known and is applicable to discrete function analogs of continuous functions is the method of finite differences. The entirety of the family of derivatives and differentials are accurately approximated by finite difference methods, particularly those methods that are based on the method of Taylor Series expansion for a function. For example, first derivatives are well approximated using the forward difference, backward difference, or central difference Taylor Series expansion methods. Other similar methods are the linear approximation methods that construct tangent and secant lines in relation to the point of local change or variation.

In one embodiment, the ULV is determined by shocking the heart at a series of predetermined times in relation to the first temporal derivative of the T-wave and at increasing or decreasing test-shock strengths. The lowest shock strength which fails to induce fibrillation is determined to be the ULV. The optimal first shock strength for programming an ICD is predicted to be incrementally greater than the ULV by about 5 J. In a second embodiment, a vulnerability safety margin method, the heart is shocked at a series of predetermined times in relation to the first temporal derivative of the T-wave, but only at a single test shock energy. If fibrillation is not induced, a safe shock strength is predicted to be incrementally greater than tested shock strength by about 5 J. This safety-margin approach does not determine the minimum (optimal) safe shock strength, but rather only ensures that the programmed shock strength is sufficient. The advantages of the safety margin method are that a sufficient first shock strength for ICDs can be determined without inducing fibrillation and that only three to four test shocks are required. Research has shown that programming first ICD shocks to 5 J above the shock strength tested in this vulnerability safety-margin strategy resulted in a first-shock success rate as good as or better than those reported for other methods of implant testing. Research has also shown that this strategy, which does not require induction of fibrillation, can be applied to at least 80% of ICD recipients. (Swerdlow CD. Implantation of cardioverter defibrillators without induction of ventricular fibrillation. *Circulation.* 2001;103:2159–64.)

In another embodiment, the intra-cardiac electrogram used for determining the derivative of the T-wave is recorded between one (or more) large intra-cardiac electrode(s) such as defibrillation coils and one (or more) extra-cardiac electrodes such as the ICD housing (commonly referred to as a "case" or "can") or the ICD housing coupled to another defibrillation electrode such as a defibrillation coil in the superior vena cava.

Regarding the method of the invention, one particular aspect is for determining a therapeutic cardiac shock strength for defibrillation, comprises the steps of:

(a) sensing a change with respect to time in the T-wave of a cardiac signal;

(b) delivering a test shock by:

(i) delivering a test shock at a test-shock strength and at a test-shock time relating to the change with respect to time of the T-wave; and (ii) sensing for cardiac fibrillation; and (c) if fibrillation is not sensed, repeating step (b) at the test-shock strength and at a different test-shock time relating to the change with respect to time of the T-wave; and (d) if fibrillation is sensed, setting the therapeutic cardiac shock strength as a function of the test-shock strength.

A more specific aspect of the method for determining an optimal programmed first-shock strength of an ICD relative to the ULV, the ICD having at least one sensing electrode and at least one shocking electrode, comprises the steps of:

(a) setting an initial test-shock strength, four offset times, and a shock strength decrement;

(b) delivering a set of up to four test shocks with the ICD to the patient, each test shock member of the set of test shocks comprising the sub-steps of:

(i) sensing an electrogram from the patient;

(ii) detecting at least one predetermined base timing point prior to the T-wave of the electrogram;

(iii) differentiating the electrogram;

(iv) detecting at least one maximum of the derivative of a T-wave;

(v) measuring at least one base time interval from the at least one base timing point to the at least one maximum derivative of a T-wave;

(vi) delivering a test shock to the patient at the test-shock strength and at a test-shock time corresponding to the base time interval plus one of the offset times;

(vii) sensing for an induction of fibrillation for a predetermined sensing time period; and (viii) if fibrillation is not sensed in step b(vii), then repeating sub-steps b(i–vii), at the same test-shock strength, up to the fourth test shock, each test shock member of the set of test shocks having a different test-shock time corresponding to a base time interval plus an offset time; and (c) if fibrillation is not sensed in step (b) by the fourth test shock, then repeating step (b) at a lower test-shock strength corresponding to the shock strength decrement, to deliver at least one additional set of up to four test shocks; and (d) if fibrillation is sensed in step (b), then:

(i) defibrillating the patient; and (ii) setting the programmed first-shock strength of an ICD at a predetermined higher level than the test-shock strength at which fibrillation was induced.

Regarding the apparatus of the invention, one aspect is an overall ICD system which delivers an optimal therapeutic cardiac shock, comprising:

(a) a plurality of electrodes, at least one electrode being adapted for sensing cardiac signals and at least one electrode being adapted for delivering shocks to the heart;

(b) a shock subsystem connected to the at least one electrode for delivering shocks and which is capable of generating test shocks and therapeutic cardiac shocks; and (c) a ULV subsystem connected to the shock subsystem and for providing test shock information to the shock subsystem, the test shock information including test-shock strength and test-shock time relating to a change in cardiac signals with respect to time, and for determining the shock strength of the therapeutic cardiac shocks as a function of the test shock strength.

Another aspect of the apparatus is a ULV subsystem for determining a therapeutic cardiac shock strength, for example with an existing ICD, comprising:

(a) a sensor for sensing the electrical activity of the heart, including a change with respect to time of the T-wave of a cardiac signal and including the presence of fibrillation;

(b) a test-shock driver for transmitting time and strength information regarding test-shocks;

(c) a controller to determine the cardiac shock strength as a function of the response (fibrillation or no fibrillation) to test-shocks of varying strengths and times.

A more specific aspect of the apparatus is an ICD system for determining and providing an optimal programmed first-shock strength based on the upper limit of vulnerability, comprising:

(a) a plurality of implantable electrodes; and (b) a shock delivery subsystem for generating and delivering shocks, connected to the electrodes; and (c) a ULV subsystem comprising;

i) a sensor, connected to the electrodes, for sensing the electrical activity of the heart, including a change with respect to time of the T-wave of a cardiac signal and including the presence of fibrillation;

ii) a timer connected to the sensor for providing a series of shock times, timed relative to the maximum derivative of the T-wave;

iii) a test shock driver, connected to the timer, for transmitting timing and amplitude information regarding T-wave, test shocks;

iv) a memory unit, connected to the test shock driver and the shock subsystem, for storing programmable values such as pacing cycle length, timing intervals, an initial shock strength, and values for incrementing and decrementing shock strength; and iv) a controller, connected to the sensor, test-shock driver, and shock subsystem for incrementally varying shock strength and the shock times, whereby the system provides a test shock having a shock strength and shock time selected by the controller, the shock subsystem delivering an initial test shock to the heart at an initial shock strength and an initial shock time and delivering subsequent test shocks to the heart by varying the shock and decreasing the shock strength, a strength decrement, until the heart is induced to fibrillate, whereby the shock strength of the test shock immediately prior to the test shock that induces fibrillation represents the ULV.

The features, benefits and objects of the invention will become clear to those skilled in the art by reference to the following description, claims and drawings.

BRIEF DESCRIPTION OF THE SEVERAL VIEWS OF THE DRAWING

FIG. 3A is an actual recording of ECG lead II, an intracardiac electrogram (EGM), and its first time derivative (EGM dV/dt).

FIG. 3B is a timing diagram that represents an expanded version of the lower two panels in FIG. 3A. It depicts the relationship between a paced cardiac cycle and test electrical shocks in accordance with a preferred embodiment of the present invention. The upper panel in FIG. 3B depicts an intra-cardiac electrogram, and the lower panel depicts its first time derivative.

DETAILED DESCRIPTION

Figure 1:
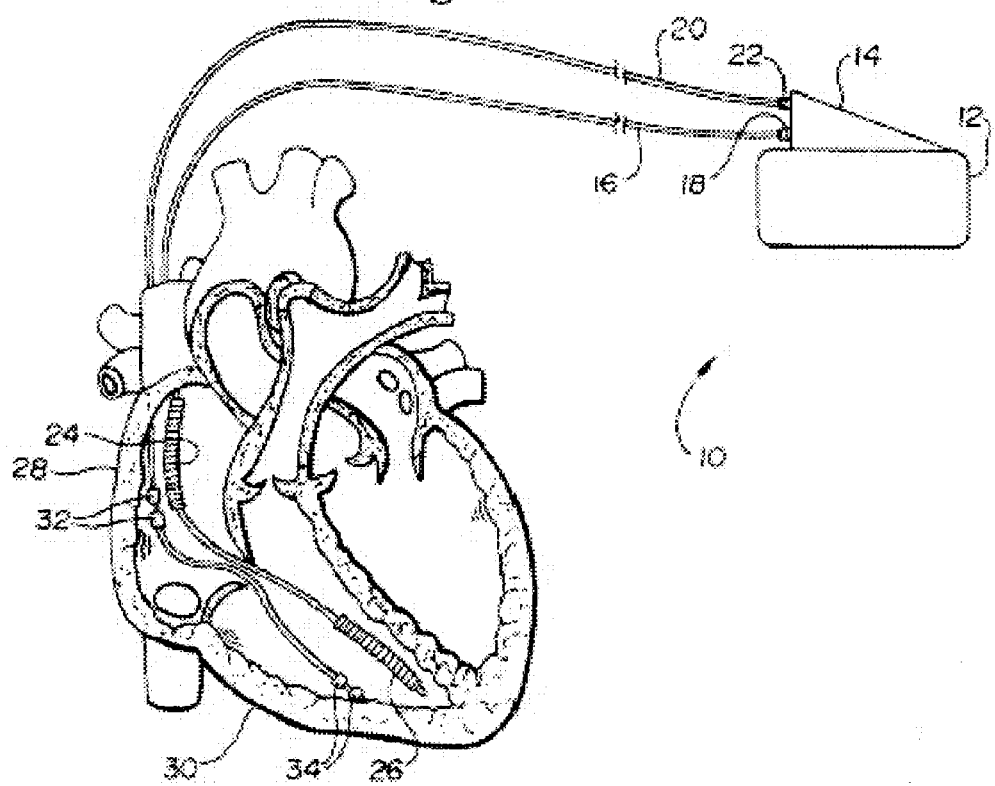
FIG. 1 is an anterior sectional view of a human heart in relative anatomical position, depicting the relative positioning of intravascular electrode catheters and an ICD according to the present invention.

Referring to FIG. 1, an embodiment of the present invention is depicted as an ICD system 10 comprising an implantable electrical pulse generating housing 12, an electrical connector pin housing 14, an implantable intravascular discharge catheter 16 electrically connected to pin housing 14 via a pin connector 18, and an implantable intravascular pacing/sensing catheter 20 electrically connected to pin housing 14 via a pin connector 22. Discharge catheter 16 carries proximal defibrillation discharge electrode 24 and distal defibrillation discharge electrode 26 and is configured to position proximal electrode 24 within right atrium 28 and position distal electrode 26 within right ventricle 30. Alternatively, these two electrodes may be on different catheters. Pacing/sensing catheter 20, carries two sets of pacing/sensing electrodes, a proximal electrode set 32 positioned within the right atrium 28 and a distal electrode set 34 positioned within the right ventricle 30. Alternatively, electrode sets 32 and 34 may be on different catheters or on the catheter that carries either or both defibrillation discharge electrodes 24 and 26. As another alternative, separate electrode pairs may be used for right-ventricular pacing and sensing. The catheters, discharge electrodes and pacing/sensing electrodes may be of any implantable design known to the art (including intracardiac, epicardial, intravascular, subcutaneous or submuscular designs). At least one defibrillation electrode must be intravascular or epicardial, with a preferred embodiment using a pacing electrode and defibrillation electrode near the right ventricular apex. Positioning of implanted pacing electrodes is preferred to be near the right ventricular apex or left ventricle, but is also not critical so long as pacer capture is reliable. This invention also permits determination of ULV without any surface electrodes.

Because DFTs vary with electrode placement and lead configuration, as well as with the responsiveness of a particular patient's heart, the ULV is determined after the electrodes and leads have been placed at their permanent positions. In this manner, the DFT corresponds to the patient and particular arrangement of the defibrillation electrodes used.

Figure 2:
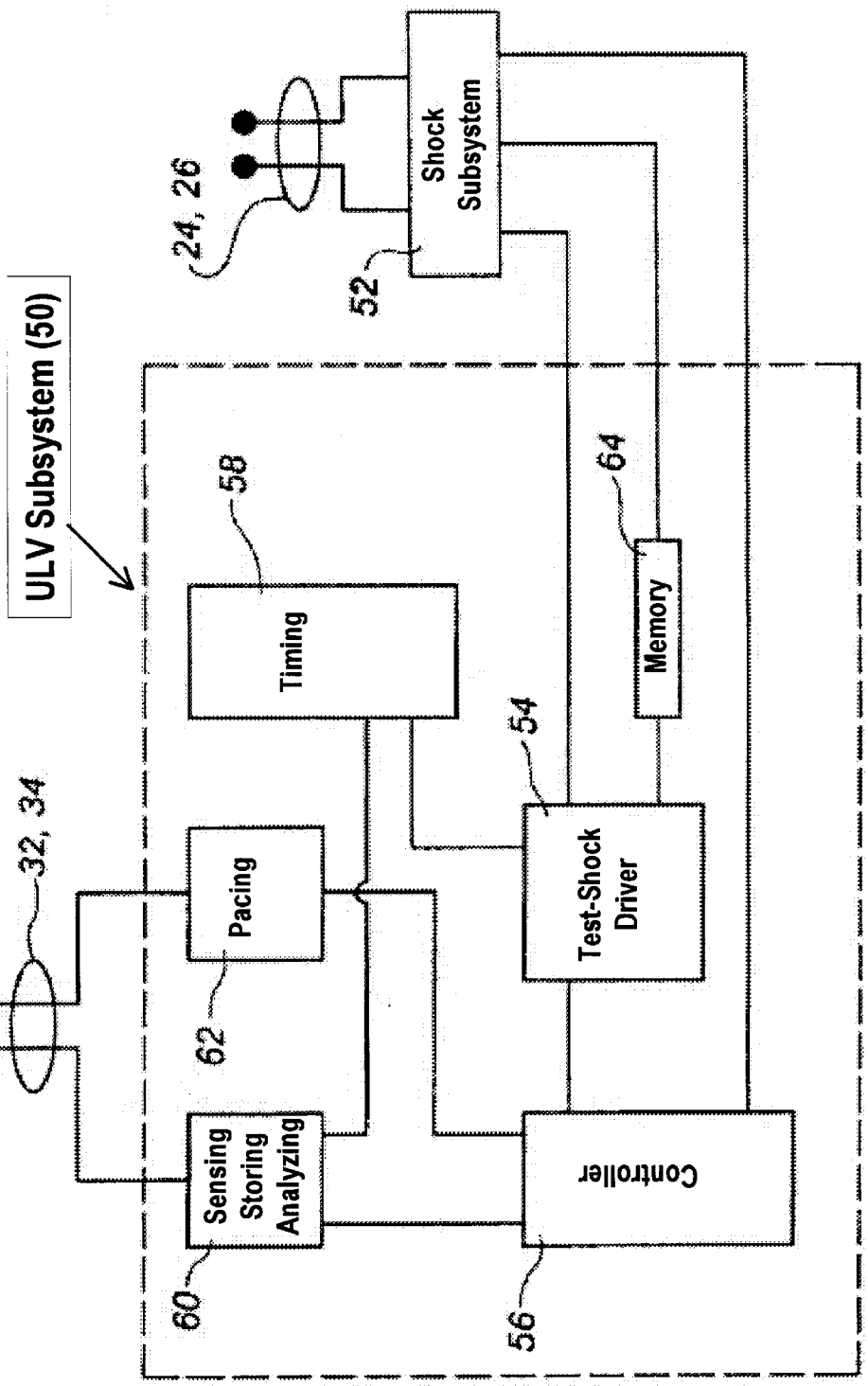
FIG. 2 is a schematic block diagram depicting a suitable arrangement for an ICD according to the present invention.

Referring to FIG. 2, an embodiment of an upper limit of vulnerability (ULV) subsystem 50 according to the present invention is depicted in one possible configuration in electrical connection with a shock subsystem 52. ULV subsystem 50 and shock subsystem 52 are component subsystems of ICD 10 of FIG. 1 and are contained within housing 12 and electrically connected. ULV subsystem 50 includes a test-shock driver for T-wave shocks 54, a test/treatment controller 56, a timing circuit 58, a sensing, storing, and analyzing circuit 60, a pacing circuit 62 (in a preferred embodiment), and a memory unit 64. Shock subsystem 52 may be of any design known to the art, but preferably is programmable to deliver either monophasic or biphasic shocks, having variable tilt, and controllable through a step wise range of energy outputs from at least 5 J to at least 30 J. Shock subsystem 52 is preferably connected to the test shock driver 54, memory 64 and controller 56 of the ULV subsystem 50. Shock subsystem 52 is used to deliver test shocks as well as defibrillation shocks. The pacing circuit 62 is not necessary for embodiments of the method and system which are operative in a native rhythm.

Figure 4:
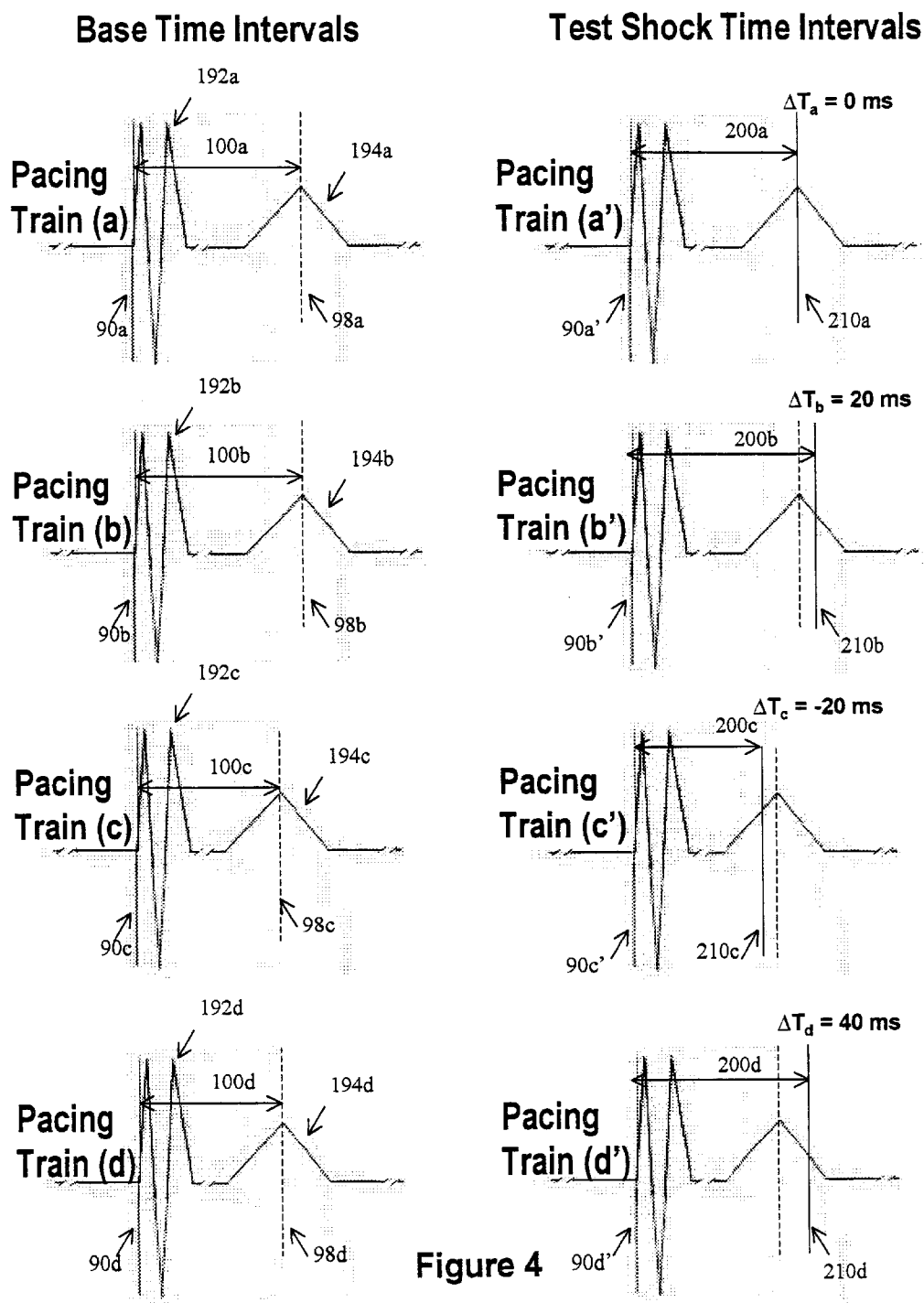
FIG. 4 is a diagram illustrating how the timing of test shocks is determined from the derivatives of an intra-cardiac electrogram for a sequence of test shocks at a single shock energy in accordance with an embodiment of the invention. Each row displays the timing measurement and corresponding shock delivery time for a single test shock.

The operation of system 10 is described in reference also to FIGS. 3B and 4. System 10 is an embodiment of the invention which utilizes pacing. The system can be modified to operate in a native rhythm as described below. Controller 56 is set to test, providing a starting test-shock strength (also called a shock-strength value or energy level), and triggering sensing circuit 60. This sensing circuit detects the heart's intrinsic rate and transmits this rate value back to controller 56. The starting shock strength is stored in memory unit 64. The intrinsic heart rate value is passed to pacing circuit 62. Pacing circuit 62 then provides a baseline pacing output through to electrode sets 32, 34 that is of a rate sufficient to overdrive the heart's intrinsic rate. Referring to FIG. 3B, the sensing, storing, and analyzing circuit 60 then evaluates the intra-cardiac electrogram 96, which represents the electrical activity of the heart, for the presence of a QRS complex 92, the derivative of the QRS complex 192, the T-wave 94, and the derivative of the T-wave 194.

The timing of the pacer spike 90 may be transmitted to the sensing circuit electronically by methods well known in the art. Alternatively, the sensing, storing, and analyzing circuit 60 may identify the pacer spike 90 during its evaluation of the intra-cardiac electrogram. The present invention anticipates an ability to evaluate the ECG or electrogram signals derived from a number of different configurations of implanted electrodes including, but not limited to, intracardiac, epicardial, intravascular, subcutaneous, and submuscular leads. Examples of sensing lead combinations may include leads positioned to record signals from the superior vena cava, the right atrium, the right ventricle, the left ventricle and combinations of electrodes such as between a lead tip electrode and a defibrillation electrode or combinations including pairing leads from the right atrium or the superior vena cava to the right or left ventricles.

Ventricular pacing is performed at a predetermined cycle length, such as 500 ms, for a predetermined duration such as 8–15 beats. The sensing and storage circuit 60 evaluates the T-waves and their time derivatives from the combinations of implanted electrodes provided during said ventricular pacing. It uses one of several algorithms for selecting a lead for timing purposes. One such algorithm is to select the lead in which the derivative of the T-wave has the latest peak.

Referring to FIG. 3A, the electrogram was recorded between right-ventricular coil and left-pectoral case plus a superior vena cava electrode. The timing of the maximum of the derivative of the T-wave ($T_{max}$) is simultaneous with the peak of the latest-peaking monophasic T-wave on the surface ECG. However, the T-wave 94 of the electrogram (EGM) is biphasic and thus could not be used for analysis by the method of Chen and Swerdlow (U.S. Pat. No. 5,564,422) referred to in the Background above. Further, the peak of the T-wave of electrogram EGM occurs much later than the peak of its derivative. Thus if any of previously-described methods that time shocks relative to the peak of the T-wave (referred to in the Background above) were applied to this electrogram, they would deliver shocks at incorrect timing intervals. This could result in a significant under-estimate of the ULV and programming ICD shock strength to an unsafe value. In contrast, the present method selects the peak 98 of the derivative of the T-wave 194 for timing purposes.

In an alternative embodiment of the apparatus of the invention, a lead is selected that provides a monophasic T-wave if one is present. If there are multiple leads with monophasic T-waves, it selects the one having the latest occurring peak with polarity opposite to that of the QRS complex. If no lead has a monophasic T-wave, it selects the lead in which the derivative of the T-wave has the latest peak.

Referring to FIG. 3B, the base time interval 100 is measured between the pacer spike 90 and the maximum (peak) 98 of the derivative of the T-wave 194. The test shock is delivered at time 210, offset from a change with respect to time in the T-wave of a cardiac signal (as is also discussed in the Summary), preferably the maximum of the derivative of a T-wave, by time $\Delta T$, and corresponding to time interval 200 after the pacer spike 90. Offset time ($\Delta T$) is defined in general as the difference between the time of the test shock ($T_{shock}$) and the time of maximum or peak of the relevant cardiac electrical signal ($T_{max}$). In the preferred embodiments, $T_{max}$ represents either the maximum of the time derivative of the T-wave or the peak of the latest-peaking monophasic T-wave that is opposite in polarity to the QRS complex or some combination thereof. A negative value of $\Delta T$ indicates a time preceding the peak. A positive value indicates a time after the peak.

Referring to FIG. 4, the left column indicates determination of four successive base time intervals 100a–d, corresponding to four different pacing sequences or trains (a)–(d). The right column indicates how these base time intervals are used to select the time intervals 200a–d of four successive test shocks at the same shock energy, delivered relative to corresponding pacing trains (a')–(d'), which may be the trains as (a)–(d) or different trains. Dashed vertical lines in both columns coincide with the maxima 98a–d of the derivatives of the T-wave. Continuous vertical lines in the right column correspond to the shock time points. In each row, the base time intervals 100a–d on the left are added to the corresponding stored values for offset times $\Delta T$a–d to calculate the shock-time intervals 200a–d, corresponding to test shock times 210a–d.

The timing circuit 58 first determines a base time interval 100a measured from the pacer spike 90a to the maximum 98a of the derivative of the T-wave 194a. The base time intervals 100a–d may be measured on one or more beats preceding the last beat of the same train of pacing pulses as the test shock. Alternatively, it may be measured on an immediately-preceding train of pacing pulses as mentioned previously. These base time intervals may be measured on a single beat or may represent the average of several beats. In one embodiment, pacing trains (a) and (a') are the same, as are (b) and (b'), (c) and (c'), and (d) and (d'). Then in FIG. 4 each row corresponds to the last two beats of successive pacing trains (a)–(d). Base time intervals 100a–d may be measured on the next to last beats of the pacing trains (following pacer spikes 90a–d), and test shocks delivered into the T-wave of the last beats of the train (following pacer spikes 90a'–d').

In one embodiment, the baseline time intervals 100a–d are measured on both the preceding pacing train (using either a single-beat or average-of-several beats) and on the current pacing train, corresponding to each of the four rows in FIG. 4, using the last beat prior to the test shock. The test shock is aborted if the difference between these two measurements is greater than a predetermined value in the range of 1–40 ms, preferably 5–20 ms, and most preferably 10 ms. This prevents delivery of test shocks in the event that the pacing train does not result in consistent capture (due to supraventricular capture beats, premature ventricular beats, or loss of capture) or the peak of the time derivative of the T-wave 194a–d is not measured consistently.

Figure 5:
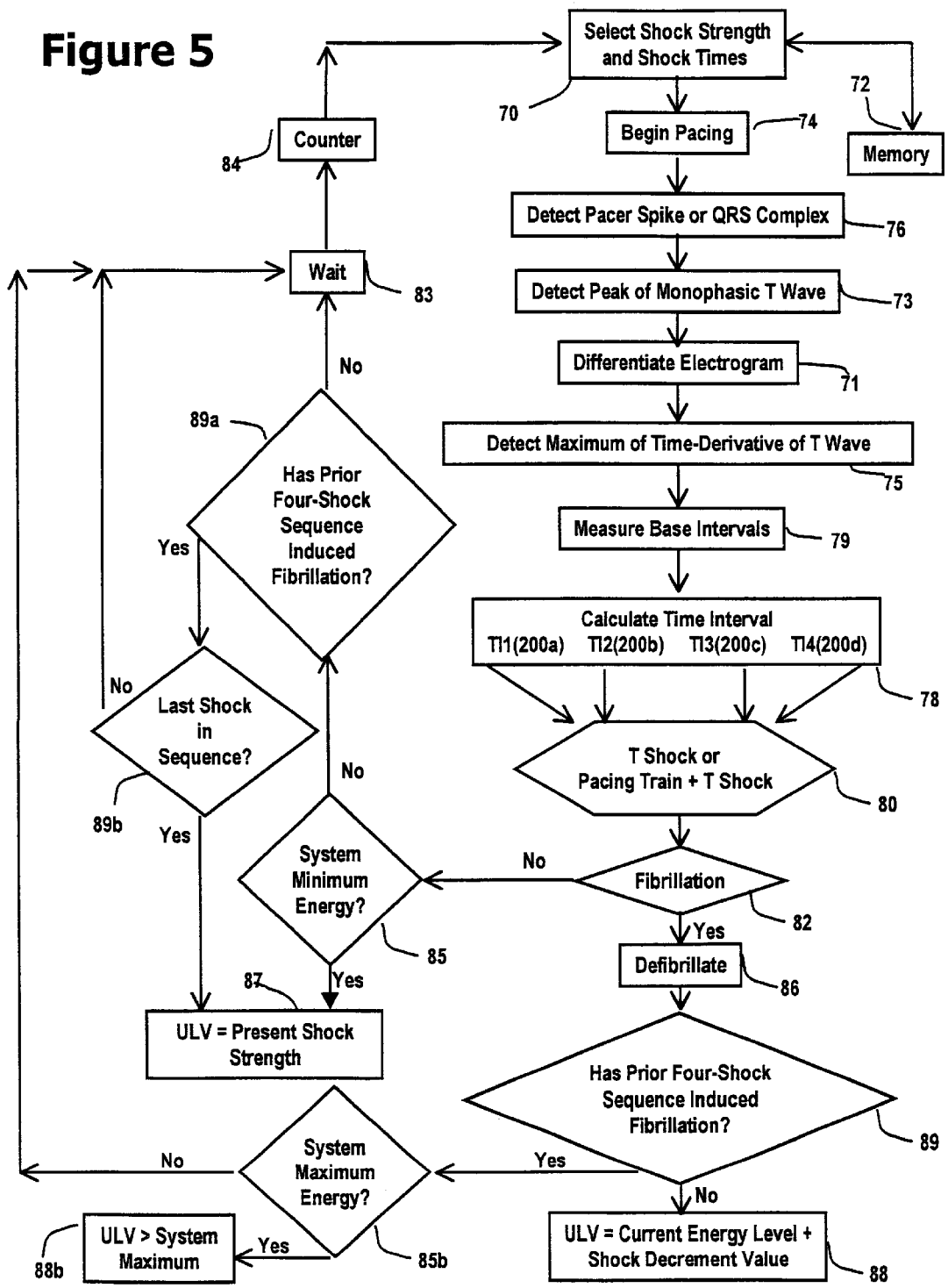
FIG. 5 is a block diagram depicting a sequence of steps in accordance with a preferred embodiment of the method and system of the present invention.

The first or starting shock-strength value and a first offset time ($\Delta$Ta) are stored in memory unit 64 and are transmitted to test-shock driver 54. The test-shock driver 54 triggers shock subsystem 52 to deliver a first test shock with the starting shock strength at a first shock time point 210a, which occurs at first time interval 200a after the next pacing spike 90a'. First time interval 200a, determined by timing circuit 58, is calculated by adding the first offset time $\Delta$Ta to the previously measured base time interval 100a. In FIG. 5 $T_{max}$ refers to the maxima 98a–d of the derivatives of the T-waves 194a–d. In an alternative embodiment, it may refer to the peak of a monophasic T-wave.

Note that the base time interval 100 shortens between pacing trains (b) and (d), but the offset times $\Delta T_{a-d}$ remain fixed relative to the maxima of the derivatives 98a–d.

The starting shock strength and offset time $\Delta$Ta–d are stored in memory unit 64 and are chosen according to a predetermined protocol. The starting shock strength is in the range of 5–30 J, preferably between 10–15 J, and most preferably 15 J. Offset time $\Delta$T may be positive, negative or zero. Offset time ranges between negative (−) 60 ms and positive (+) 40 ms and is preferably −20 ms to +40 ms for a standard three-electrode defibrillation configuration (right-ventricle to case plus superior vena cava). At least one offset time is stored and preferably four (4) in the preferred embodiment. The initial value of offset time $\Delta$T is preferably about 0 ms whereby the initial test shock is delivered such that it substantially coincides with the maximum of the derivative of the T-wave following the next pacer spike 90a'.

In an alternative normal-rhythm embodiment of the apparatus, time delays are calculated in a similar fashion, except that they are based on measurements made in normal rhythm. A time interval is calculated based on the interval between the detected QRS complex (as opposed to a pacer spike) and the peak of the time derivative of the selected intra-cardiac T-wave.

In most cases, the initial test shock energy is sufficiently strong such that fibrillation is not induced. After delivery of the first test shock, pacing from the pacing circuit 62 is turned off and the cardiac rhythm is monitored by the sensing and storage circuit 60 for the presence of fibrillation.

If fibrillation is not induced by the first test shock, controller 56 waits a predetermined period of time, preferably about one (1) minute, before starting the next test shock. During this and all subsequent waiting periods, a pacing train (in this case train (b)) may be delivered and analyzed by sensing and storage circuit 60. This analysis updates interval 100 based on the timing of the maximum of the derivative of the intra-cardiac T-wave. This updated interval 100 is stored in timing circuit 58 for the next test-shock pacing sequence. Alternatively, sensing and storage circuit 60 may analyze the timing of the maximum of the derivative of the intra-cardiac T-wave during the paced beats of each pacing train and that value may be used to determine the timing of the shock at the end of the same pacing train. In this case, no pacing train is delivered during the waiting period, and the value of interval 100 is not updated until the waiting period ends and the test-shock's pacing train begins. In either case, these additional measurements result in updated measurements 100b–d of the base time interval 100 for each successive test shock in the sequence as shown in FIG. 4.

After the first test shock and monitoring and waiting period, controller 56, is programmed to deliver up to three additional sequences (a total of four) of ventricular pacing at a predetermined cycle length for a predetermined number of beats followed by test shocks at the same starting shock strength (a total of four test shocks), at different intervals 200b–d corresponding to times 120b–d, followed by additional monitoring and waiting periods.

For the second test shock in the first round of test shocks, timing circuit 58 determines a second time interval 200b from the pacer spike 90b, corresponding to the base time interval 100b plus a second $\Delta$Tb 210b which is preferably plus 20 ms. The heart is shocked at the end of this interval 200b, which occurs at second shock time point 200b, which falls 20 ms after the maximum derivative 98b of the T-wave 194b.

If fibrillation is not induced, the controller 56 waits the predetermined wait period before initializing the chain of events leading to the third test shock at the first shock strength and commences with timing circuit 58 determining a third time interval 200c from pacer spike 90c corresponding to base time interval 100c plus third $\Delta$Tc which is preferably minus 20 ms. The heart is shocked at the end of this interval 200c, which occurs at third time point 210c which is preferably 20 ms before maximum derivative 98c of the T-wave 194c and the heart is shocked again.

If fibrillation is not induced by the third test shock, the controller 56 waits the predetermined wait period before initializing the chain of events that results in a fourth test shock at the first shock strength. Timing circuit 58 determines a time interval 200d from pacing spike 90d corresponding to the base interval 100 plus a fourth $\Delta$Td which is preferably plus 40 ms. The resultant shock time point 210d that is preferably 40 ms after the maximum 98d derivative of the T-wave 194d. After each test shock the cardiac rhythm is monitored by the sensing circuit 60 to ascertain if the shock has induced fibrillation. If fibrillation is not induced, the controller 56 waits the predetermined wait period before delivering the next test shock.

In the example shown in FIG. 4, base time interval 100 shortens between the times of the second and third rows so that base intervals 100c and 100d are shorter than base intervals 100a and 100b. Similarly, shock timing intervals 200c and 200d are shorter than shock timing intervals 200a and 200b. However, the offset intervals $\Delta$Tc and $\Delta$Td remain appropriately timed relative to the peaks of their corresponding derivatives 194c and 194d. Although this illustration shows only one change in base time interval 100, any change in this base time interval is accompanied by a corresponding change in the shock-time interval 200.

If fibrillation is not induced by a series of four T-wave shocks at the same shock strength shock and different intervals 200a–d, controller 56 lowers the shock strength by a predetermined test-shock strength decrement value which is also stored in memory unit 64 and set by a predetermined protocol. The controller 56 waits the predetermined wait period before transmitting the newly determined, second test-shock strength to the test-shock driver 54 and then to shock subsystem 52 after the predetermined waiting period. This initiates a second series of up to four test shocks. The first test shock in the second round is delivered at a first time point corresponding to a first timing interval determined by timing circuit 58 after a pacing spike 90. Preferably, all of the time offsets ΔT in the second round are equivalent to those in the first test shock sequence. However, one or more of the time offsets may be varied. The amount by which the second test-shock strength is reduced relative to the first shock strength (i.e. the shock energy decrement value) is in the range of 1–10 J, usually in the range of 2–5 J. The preferred decrement value is about 5 J at test-shock strengths of 10 J or greater and about 2 J at test-shock strengths of about 5 J or less. The specific values may be selected from one of various testing strategies, including those used for selecting shock decrement values for DFT testing. The sequence of test shocks in the second sequence is repeated in the same manner as that described with respect to the starting sequence until fibrillation is induced.

If fibrillation has not been induced after the second round of test shocks, one or more subsequent rounds of test shocks may be administered until the system minimum level shock strength, typically 2 J–5 J, is reached. Each subsequent round preferably has the same maximum number of test shocks, each delivered at the same corresponding time offsets ΔT relative to the end of time interval 100, which is updated prior to each test shock . The test-shock strength of the next round is determined by lowering the shock strength of the previous round by a decrement value that in general is specific to the shock value corresponding to the previous round. Therefore, in this embodiment, for each test-shock strength, there is a set of up to four test-shocks, corresponding to each of the four shock time points 210*a–d*, calculated by adding an offset times ΔTa–d to base time intervals 100*a–d*. In a preferred embodiment, time intervals 200*a–d* are calculated based on electrogram measurements made in paced rhythm.

If a test shock in any shock sequence induces fibrillation then the shock strength of the last shock sequence in which no shock induced fibrillation (i.e. the shock strength of the prior shock sequence) may be accepted as the step-down ULV (which is an accurate estimate of the DFT). If fibrillation has not been induced even at the system minimum, 1–5 J level as determined in step 85, the ULV is calculated to be the minimum tested shock strength in step 87; and the defibrillation shock strength is set to a level incrementally above the ULV, preferably with an increment of at least 5 J.

In the safety-margin embodiment referred to previously, testing is limited to the first round or sequence of four shocks at a single shock strength if fibrillation is not induced. No second or subsequent round is utilized. The first ICD shock is then programmed incrementally above this value.

As was discussed above, in most cases the initial test shock energy is sufficiently strong such that fibrillation is not induced. The present invention anticipates that a small fraction of patients will fibrillate in response to the first shock strength. Referring to FIG. 5 , this condition is identified in step 89. If this occurs, the test-shock strength is incremented to a next higher shock strength in step 70 based on data stored in memory 72 and testing is repeated. As noted above, this testing consists of pacing the heart for a predetermined number of beats, delivering a shock at a predetermined time interval after the last pacer spike, observing for the induction of fibrillation, and if fibrillation is not induced iterating this process at up to three other time intervals. If fibrillation is not induced by any shock at this higher shock strength, step 89*a* determines that fibrillation has been induced at least once. Step 89*b* then determines if the present shock is the last shock in a four-shock sequence. If it is, the ULV is set equal to this value in step 87. If the present shock is not the last shock in a four-shock sequence, step 89*b* continues the testing sequence.

If fibrillation is induced, step 85*b* again determines if the present shock value equals the system maximum shock strength. If it does not, waiting period 83 is reinitiated, counter 84 is reset to 1, and the shock strength is incremented to the next higher value in step 70 based on data stored in memory 72. The testing process is iterated until a shock strength is reached at which fibrillation is not induced by any of four test shocks as determined by step 89*b*. This shock strength is set equal to the ULV in step 87. If test shocks at the maximum system energy induce fibrillation, the ULV is determined to be greater than this value in step 88*b*. In this case, the ICD system usually is revised by changing electrodes, shock waveform or polarity, maximum system energy, or some other parameter.

Alternative embodiments may provide more accurate estimates of a shock strength associated with a specific probability of defibrillation success, but they require additional fibrillation-defibrillation episodes. These involve the concept of multiple reversals between shock strength that do not induce fibrillation and those that do induce fibrillation analogous to the reversal of response methods for determining the DFT. Methods that utilize a specific number of equal-size reversal steps or a Bayesian method for selecting unequal steps can be applied to ULV testing as well as to DFT testing. They provide a more accurate estimate of a specific point of the defibrillation probability of success curve.

In one embodiment, the baseline time intervals 100*a–d* are measured on both the preceding pacing train (using either a single-beat or average-of-several beats) and on the current pacing train, corresponding to each of the four rows in FIG. 5, using the last beat prior to the test shock. The test shock is aborted if the difference between these two measurements is greater than a predetermined value in the range of 1–40 ms, preferably 5–20 ms, and most preferably 10 ms. This prevents delivery of test shocks in the event that the pacing train does not result in consistent capture (due to supraventricular capture beats, premature ventricular beats, loss of capture) or the peak of the time derivative of the T-wave 194*a–d* is not measured consistently.

While the above embodiments are implemented in an ICD, the invention can also be implemented in an ICD programmer or an independent external device for testing defibrillation efficacy. Such a device may be referred to as "an implant-support device."

When the invention is implemented in a programmer or implant-support device, surface ECG leads, one or more electrograms including the electrogram that is differentiated, and the differentiated signal may be displayed on a computer screen to be viewed by an operator. The timing points 90*a–d*, and 98*a–d* and timing intervals 100*a–d* may also be displayed on the computer screen. In one embodiment test shocks are not delivered unless the operator confirms the automatically-selected timing points and intervals. The operator may alter the timing points and intervals manually using an input device such as a mouse, trackball, touchscreen pen, or other such input devices that are well known in the art. This operator-assisted method of selecting timing points and intervals may also be used with an ICD. In this embodiment, the electrograms, differentiated electrograms, timing points and timing intervals are sent from the ICD to the programmer via telemetry, and the programmer telemeters the confirmation signal or modifications of the timing points and intervals to the ICD prior to delivery of the test shock. In these operator-assisted embodiments, the baseline time intervals 100a–d are measured on one preceding pacing train and the test shocks are delivered on a subsequent pacing train.

Referring also to FIG. 5, a preferred embodiment of the method of the present invention begins with step 72 wherein a first or starting test-shock strength, one or more offset time intervals ($\Delta T$), and one or more test-shock strength decrement value(s) are stored in and retrieved from memory unit 64 of the ULV subsystem 50. The starting shock strength, shock decrement value, and offset times $\Delta T$ are chosen according to a predetermined protocol. As was discussed above with respect to the apparatus of the invention, the preferred first shock strength is in the range of 10–15 J, but may range from 5 J to 30 J. The preferred number of shocks is four (4). Therefore, in this embodiment, for each test-shock strength there is a set of up to four test shocks corresponding to each of the four shock time points 210a–d. Each test-shock time 210a–d, falls at the end of time intervals 200a–d, after a respective pacing spikes 90a–d'. The time intervals 210a–d, 210b, 210c and 210d are calculated by adding an offset times $\Delta Ta$–d to base time intervals 100a–d. The base time 100a–d is the time between the pacing spike 90a–d to the maximum derivative of the T-wave 194a–d in the electrogram 192a–d proceeding electrograms 192a–d. In a preferred embodiment of the invention, time intervals 200a–d are calculated based on electrogram measurements made in paced rhythm.

However, these shock-time intervals may alternatively be based on measurements made in normal rhythm as described below. In the preferred embodiment, step 74 initiates overdrive pacing of the heart. One method for selecting intervals in paced rhythm is shown in step 73. This method may be applied only if a recorded electrogram has a suitable monophasic T-wave.

In step 76, pacing is confirmed and electrograms are recorded. In step 73, the peak of the latest peaking monophasic T-wave is identified by analyzing electrogram morphology in each recorded lead. The preferred method for selecting intervals in paced rhythm is shown in steps 71, 75, and 77. This method can be applied regardless of whether a monophasic T-wave is present. In step 71, the electrograms recorded and analyzed in step 76 are differentiated with respect to time. In step 75, the maximum of the time derivative of the T-wave is determined from the first time derivative of each electrogram 196a, the latest of these peaks 98a is selected, and base time 100a is calculated from the pacer spike 90a to such peak 98a. In step 78, a shock-time interval 200a is calculated by adding one of a predetermined time offset intervals $\Delta T$ stored in step 72 to the base interval 100a determined in step 75. $\Delta T$ may be positive, negative, or zero. Offset time $\Delta T$ ranges between negative (−) 60 ms and positive (+) 40 ms and is preferably −40 ms to +20 ms. The initial $\Delta Ta$ is preferably about 0 ms. In the preferred embodiment, first time interval 200a is calculated based on $\Delta Ta$ of 0 ms. It starts at the time of pacing spike 90a' and ends at shock-time point 210a, which occurs substantially simultaneously with the latest maximum peak of the derivative of the T-wave. As FIG. 3A shows, it is also substantially simultaneous with the peak of the latest-peaking monophasic T-wave on the surface ECG. In subsequent cycles of step 78, where applicable, second, third and fourth intervals may be calculated. Second time interval 200b is based on $\Delta Tb$ of +20 ms and begins at pacer spike 90b and yields shock time point 210b which is approximately 20 ms after the maximum 98b of the derivative of the T-wave 194b. Third time interval 200c is based on $\Delta Tc$ of −20 ms, begins at pacer spike 90c and yields third time point 210c which is about 20 ms before the maximum 98c of the derivative of the T-wave 194c. The fourth interval 200d is based on $\Delta Td$ of +40 ms, begins at pacer spike 90d and yields fourth shock time point 210d which is about 40 ms after the maximum 98d of the derivative of the T-wave 194d.

Then after the next suitable pacer spike 90a', step 80 initiates a first test shock which is delivered to the heart after first interval 200a calculated in step 78. Following first test shock, pacing is turned off in the embodiment utilizing pacing, and the heart is monitored for the induction of fibrillation at step 82. As was discussed above in connection with the apparatus of the invention, in most cases, the initial test shock energy is sufficiently high such that fibrillation is not induced. If no fibrillation is detected, step 83 involves waiting a predetermined period of time of approximately one (1) minute, and a counter is incremented at step 84. Subsequently, the process is repeated beginning at selection step 70 selecting the next offset time T and utilizing the same (first) shock strength. The process may be repeated up to a predetermined maximum number of shocks, preferably four (4), in a round or sequence, at the first test-shock strength. Since the first shock strength is selected such that it is too high to induce fibrillation in most patients, usually a second sequence or round of one or more test shocks up to the predetermined maximum number per round will be initiated, at preferably the same shock-time delays, but at a lower shock strength.

After the first sequence of a preselected number of test shocks at the same energy, the counter has reached the predetermined maximum, in this case four. Then step 84 resets the counter to one. This causes step 70 to determine a new test-shock strength based on adding the predetermined shock decrement value stored in step 72, preferably 5 J, to the existing test-shock strength used in step 70. The second round or sequence of test shocks then delivers shocks in the same manner as that described above with respect to the first sequence. If after the second round of test shocks, fibrillation has not been induced, one or more additional rounds of test shocks are administered provided the system minimum level of shock strength, typically 5 J, has not been reached as determined in step 85. Each subsequent round utilizes a lower shock strength from that value used in the previous round at step 70 based on the shock decrement value. If fibrillation has not been induced even at the system minimum, 5 J level as determined in step 85, the ULV is calculated to be equivalent to 5 J in step 87, and the defibrillation shock strength is set to a level incrementally above the ULV.

In an alternative normal rhythm embodiment of the method, time delays are calculated in a similar fashion, except that they are based on measurements made in normal rhythm or atrial-paced rhythm. A time interval is calculated based on the interval between the detected QRS complex (as opposed to a pacer spike) and the peak of the time derivative of the selected intra-cardiac T-wave. In the alternative normal rhythm embodiment, step 76 also includes the sub-step of determining that the heart's rhythm is sufficiently regular that the time interval between the detected QRS complex and the peak of the derivative of the intra-cardiac T-wave is likely to be substantially constant over a few beats.

The principal advantage of the present invention is the capacity to automate determination of the optimal first shock strength for transvenous ICDs using only implanted electrodes by determining the ULV with improved accuracy, safety, speed and simplicity. The present invention is substantially improved over previous methods of determining the ULV for purposes of predicting the DFT and is of sufficient accuracy that conventional DFT testing is unnecessary. The time required for the procedure is substantially shortened by diminishing the number of episodes of fibrillation, the number of shocks in regular rhythm, the need to record a 12-lead surface ECG, and the need to make cumbersome measurements from the 12-lead surface ECG. The present invention is easy to apply because all measurements can be automated in the software of the ICD or programmer.

Figure 6:
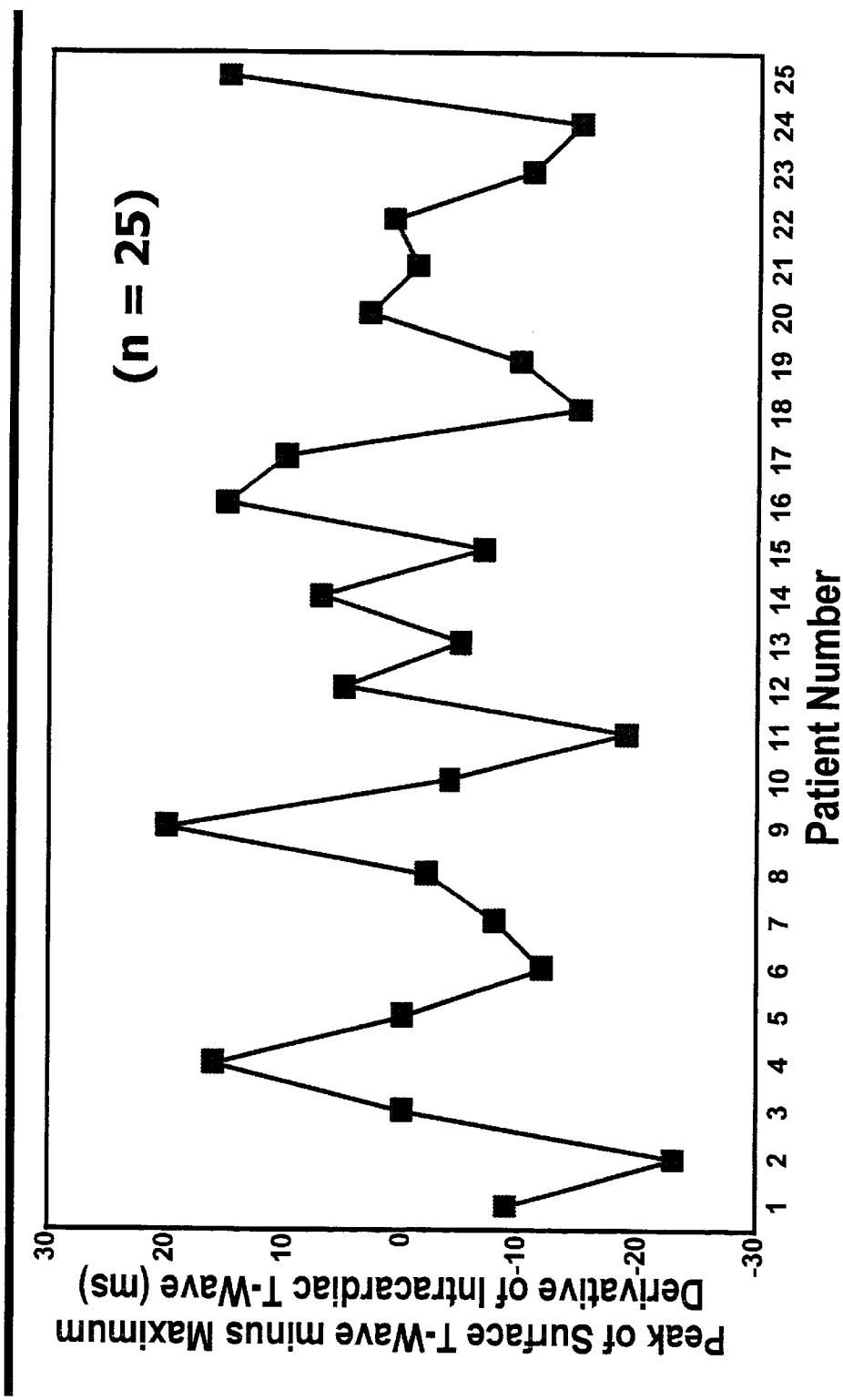
FIG. 6 is a graph that compares the timing of the peak of the latest peaking monophasic T-wave on the surface ECG with the timing of the maximum derivative of the T-wave determined from ICD electrodes.

FIG. 6 is a graph that compares the timing of the peak of the latest peaking monophasic T-wave on the surface ECG with the timing of the maximum derivative of the T-wave determined from ICD electrodes. The ordinate shows the timing difference (in ms) between the peak of the latest-peaking T-wave on the surface ECG and timing of the maximum derivative of the T-wave recorded from totally-implanted ICD electrodes. The abscissa represents 25 consecutive patients studied at ICD implant. The electrogram is recorded from either a two-electrode shocking configuration (right-ventricular coil to left-pectoral case) or a three-electrode shocking configuration (right-ventricular coil to left-pectoral case plus a superior vena cava electrode). The mean difference was 2 ms with a standard deviation of 11 ms. The maximum absolute difference for an individual-patient was 23 ms.

Figure 7:
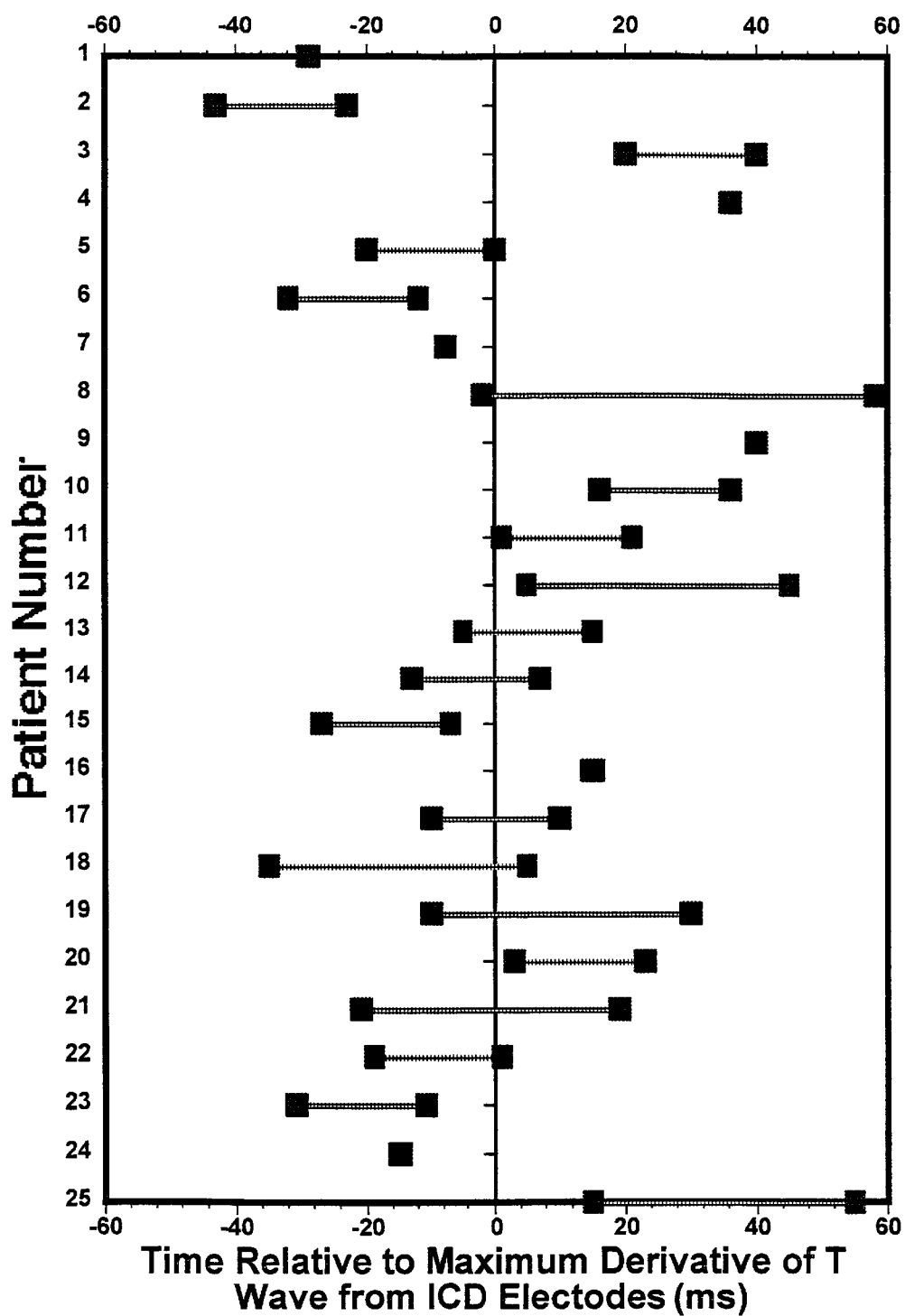
FIG. 7 shows the timing of the most vulnerable intervals, representing the peak of the vulnerable zone, in relation to the timing of the maximum derivative of the T-wave determined from ICD electrodes.

FIG. 7 shows the timing of the most vulnerable intervals, representing the peak of the vulnerable zone, in relation to the timing of the maximum derivative of the T-wave (corresponding to time 0) determined from the same 25 patients shown in FIG. 6. The range of −20 to +40 ms relative to the maximum derivative of the T-wave includes the peak of vulnerable zone in 24 patients (96%). For Patient 1, the peak of the vulnerable zone precedes the maximum derivative of the T-wave by 29 ms. Note that the peak of the vulnerable zone is relatively narrow with both mean and median width of 20 ms. It includes only one two 20-ms intervals in 80% of patients. Thus, if only one or two T-wave shocks are given (as recommended in previous methods discussed in Background section), small errors in their T-wave shocks can result in erroneous measurement of the ULV.

The descriptions above and the accompanying drawings should be interpreted in the illustrative and not the limited sense. While the invention has been disclosed in connection with an embodiment or embodiments thereof, it should be understood that there may be other embodiments which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A method for determining a cardiac shock strength, comprising the steps of:
   (a) sensing a change with respect to time in a T-wave of an electrical cardiac signal, the change with respect to time being a derivative of T wave amplitude with respect to time;
   (b) delivering a test shock by:
      (i) delivering a test shock at a test-shock strength and at a test-shock time relating to sensing the derivative of T wave amplitude with respect to time; and
      (ii) sensing for cardiac fibrillation; and
   (c) if fibrillation is not sensed, repeating step (b) at the test-shock strength and at a different test-shock time relating to the derivative of T wave amplitude with respect to time; and
   (d) if fibrillation is sensed, setting the cardiac shock strength as a function of the test-shock strength.

2. The method of claim 1, wherein the change with respect to time is selected from the group consisting of a finite difference, an ordinary derivative, a directional derivative, a gradient, a partial derivative, an implicit differential, a variance calculation, a bounded variation calculation, a radial displacement vector, and a tangent vector approximation.

3. The method of claim 1, wherein the change with respect to time is an extreme value calculated by a method selected from the group consisting of a finite difference, an ordinary derivative, a directional derivative, a gradient, a partial derivative, an implicit differential, a variance calculation, a bounded variation calculation, a radial displacement vector, and a tangent vector approximation.

4. The method of claim 1, wherein the change with respect to time is a maximal value calculated by a method selected from the group consisting of a finite difference, an ordinary derivative, a directional derivative, a gradient, a partial derivative, an implicit differential, a variance calculation, a bounded variation calculation, a radial displacement vector, and a tangent vector approximation.

5. The method of claims 1, wherein the change with respect to time is a derivative of T-wave amplitude with respect to time selected from the group consisting of the first derivative, second derivative, third derivative, and nth derivative.

6. The method of claim 5, wherein the change with respect to time is the first derivative of T-wave amplitude with respect to time.

7. The method of claim 1 in which test-shock times are selected in relation to the maximum of the first derivative of the T-wave with respect to time.

8. The method of claim 1, wherein step (b) is performed in native rhythm of the heart, further comprising the step of sensing a QRS complex of the cardiac signal via an implanted ventricular sensing or pace/sense electrode, and wherein the test-shock time is further based on the sensed QRS complex of the cardiac signal.

9. The method of claim 1, wherein step (b) is performed in atrial-paced rhythm of the heart, further comprising the steps of pacing the rhythm of the heart via an implanted atrial pacing or pace/sense electrode and sensing a QRS complex of the cardiac signal, and wherein the test-shock time is further based on the sensed QRS complex of the cardiac signal.

10. The method of claim 1, wherein step (b) is performed in ventricular-paced rhythm of the heart, further comprising the step of delivering a pacer spike via an implanted ventricular pacing or pace/sense electrode, and wherein the test-shock time is further based on the pacer spike.

11. The method of claim 1, wherein step (b) is performed in atrioventricular-paced rhythm of the heart, further comprising the step of delivering a ventricular pacer spike from implanted pacing or pace/sense electrodes, and wherein the test-shock time is further based on the ventricular pacer spike.

12. The method of claim 1, further comprising the step of recalculating the test-shock time in accordance with step (a) and (b)(i) if fibrillation is not sensed.

13. The method of claim 1, wherein each test-shock time is predetermined.

14. The method of claim 1, wherein step (b) is repeatable a maximum number of times, and wherein if fibrillation is not sensed at the maximum number, a therapeutic cardiac shock strength is set as a value greater then the test-shock strength.

15. The method of claim 1, wherein step (b) is repeatable a maximum number of sequence times, and wherein if fibrillation is not sensed at the maximum number, the test-shock strength is decreased by an amount and steps b–c are repeated in a new sequence.

16. The method of claim 15, wherein the changed amount is based on at least one of the outcomes from a previous sequence of test shocks.

17. The method of claim 15, determining the changed amount based on at least one of the outcomes from the previous sequence of test shocks.

18. The method of claim 15, determining the changed amount based on at least one of the outcomes from the previous sequence of test shocks and taken by a method from the group of methods consisting of including "up-down" and Bayesian methods.

19. The method of claim 18, wherein, if fibrillation is not sensed at a predetermined minimum shock strength, further comprising the step of setting the cardiac shock strength at the predetermined minimum shock strength.

20. The method of claim 15, wherein the changed amount is a function of the test-shock strength.

21. The method of claim 15, wherein the changed amount is a predetermined value.

22. The method of claim 1, wherein the cardiac shock strength is a function of the lowest test-shock strength that does not induce fibrillation.

23. The method of claim 22, wherein the function is 5J more than the lowest test-shock strength that does not induce fibrillation.

24. A method for determining a cardiac shock strength for a medical device connected to a patient and capable of delivering a shock, comprising the steps of:
(a) delivering a set of test shocks with the device connected to the patient, each member of the set comprising the sub steps of:
  (i) sensing an electrogram from the patient;
  (ii) detecting the maximum derivative of a T-wave of the electrogram;
  (iii) delivering a test shock to the patient at a test-shock strength and at a test-shock time relating to the maximum derivative of the T-wave;
  (iv) sensing for induction of cardiac fibrillation; and
  (v) if fibrillation is not sensed in step a(iv), then repeating sub-steps a(i–iv) at the test-shock strength up to a predetermined maximum set number, each member of the set having a different test-shock time relating to the maximum derivative of the T-wave; and
(b) if fibrillation is not sensed in step (a) after the maximum set number, then repeating step (a) at a lower test-shock strength; and
(c) if fibrillation is sensed in step (a), then defibrillating the patient and setting the cardiac shock strength as a predetermined function of the test-shock strength that induced fibrillation.

25. A method for determining an optimal programmed first-shock strength of an implantable cardioverter defibrillator, comprising the steps of:
(a) delivering a set of test shocks having a predetermined maximum number of members with the cardioverter defibrillator to the patient, each member of the set comprising the sub steps of:
  (i) sensing an electrogram from the patient;
  (ii) differentiating the electrogram;
  (iii) detecting the maximum of the derivative with respect to time of a T-wave of an electrogram;
  (iv) delivering a test shock to the patient at a test-shock strength and at a test-shock time relating to the maximum of the derivative with respect to time of the T-wave;
  (v) sensing for an induction of cardiac fibrillation; and
  (vi) if fibrillation is not sensed in step a(v), then repeating sub steps a(i–v) at the same test-shock strength up to a predetermined maximum set number, each member of the set having a different test-shock time relating to the maximum of the derivative of the T-wave with respect to time; and
(b) if fibrillation is not sensed in step (a) after the maximum set number, then repeating step (a) at a lower test-shock strength; and
(c) if fibrillation is sensed in step (a), then defibrillating the patient and setting the programmed first-shock strength of an ICD at a predetermined higher level than the test-shock strength that induced fibrillation.

26. A method for determining an optimal programmed first-shock strength of an implantable cardioverter defibrillator, comprising the steps of:
(a) delivering a set of up to five test shocks with the cardioverter defibrillator to the patient, each test shock member of the set of test shocks comprising the sub steps of:
  (i) sensing an electrogram from the patient;
  (ii) differentiating the electrogram;
  (iii) detecting the maximum of the first derivative with respect to time of a T-wave of an electrogram;
  (iv) delivering a test shock to the patient at a test-shock strength and at a test-shock time relating to the maximum of the first derivative of the T-wave with respect to time;
  (v) sensing for an induction of cardiac fibrillation; and
  (vi) if fibrillation is not sensed in step a(v), then repeating sub steps a(i–v) at the same test-shock strength up to and including the last of up to five test shocks, each test shock member of the set of test shocks having a different test-shock time relating to the maximum of the first derivative of the T-wave with respect to time; and
(b) if fibrillation is not sensed in step (a) by the last of up to five test shocks, then repeating step (a) at a lower test-shock strength, to deliver at least one additional set of up to five test shocks; and
(c) if fibrillation is sensed in step (a), then:
  (i) defibrillating the patient with the implantable cardioverter defibrillator; and
  (ii) setting the optimal programmed first-shock strength of an ICD of the implantable cardioverter defibrillator at a predetermined higher level than the test-shock strength at which fibrillation was induced.

27. A method for determining an optimal programmed strength of a first therapeutic shock of an implantable cardioverter defibrillator relative to the upper limit of vulnerability, the implantable cardioverter defibrillator having at least one sensing electrode, at least one pacing electrode, and at least one shocking electrode, comprising the steps of:

(a) setting an initial test-shock strength, up to four offset times, and a shock strength decrement;

(b) delivering a set of up to four test shocks with the implantable cardioverter defibrillator to the patient, each test shock member of the set of test shocks comprising the sub steps of:

(i) sensing an electrogram from the patient;

(ii) detecting at least one predetermined base timing point prior to the T-wave of the electrogram;

(iii) differentiating the electrogram with respect to time;

(iv) detecting at least one maximum of the first derivative with respect to time of a T-wave of the differentiated electrogram;

(v) measuring at least one base time interval from the at least one base timing point to the at least one maximum of the first derivative with respect to time of a T-wave;

(vi) delivering a test shock to the patient at the test-shock strength and at a test-shock time corresponding to the base time interval plus one of the offset times;

(vii) sensing for an induction of cardiac fibrillation for a predetermined sensing time period;

and (viii) if fibrillation is not sensed in step b(vii), then repeating sub steps b(vii), at the same test-shock strength, up to the fourth test shock, each test shock member of the set of test shocks having a different test-shock time corresponding to a base time interval plus an offset time; and (c) if fibrillation is not sensed in step (b) by the fourth test shock, then repeating step (b) at a lower test-shock strength corresponding to the shock strength decrement, to deliver at least one additional set of up to four test shocks; and (d) if fibrillation is sensed in step (b), then:

(i) defibrillating the patient; and (ii) setting the programmed first-shock strength of the implanted cardioverter defibrillator at a predetermined higher level than the weakest test-shock strength at which fibrillation was not induced, which test-shock strength represents the upper limit of vulnerability.

28. The method of claim 27, further comprising the step, after step (d), of repeating steps (c) and (d) a specified number of times.

29. The method of claim 28, in which the shock strength decrement is a function of the initial test-shock strength.

30. The method of claim 28, in which the specified number of times is between 0 and 10.

31. The method of claim 28, in which the specified number of times is 2 or 3.

32. The method of claim 28, in which the specified number of times depends on the outcomes with respect to fibrillation of all previous test shocks delivered.

33. The method of claim 28, further comprising the sub step of waiting a predetermined period of time before repeating step (b) at a higher test-shock strength.

34. The method of claim 28, delivering a sequence of one or more test shocks at only one shock strength, and if fibrillation is not detected in step (b) by the fourth test shock, setting the programmed shock strength of the implantable cardioverter defibrillator to a value that is a fixed increment greater than the test shock strength.

35. The method of claim 27, implementing the sensing and detecting steps entirely with signals obtained from the sensing electrode and the shocking electrode, the sensing electrode and the shocking electrode both being implanted.

36. The method of claim 35, wherein at least one said implanted electrode is an intracardiac electrode.

37. The method of claim 35 wherein at least one said implanted electrode is an intravascular electrode.

38. The method of claim 35, wherein at least one said implanted electrode is a subcutaneous electrode.

39. The method of claim 35, wherein at least one said implanted electrode is a submuscular electrode.

40. The method of claim 35, wherein at least one said implanted electrode is an epicardial electrode.

41. The method of claim 27, wherein at least one said sensing electrode is externally disposed.

42. The method of claim 27, wherein the initial shock strength is a sufficiently physiologically high energy value that it is not likely to cause fibrillation.

43. The method of claim 27, wherein the initial shock strength is in the range of 5–30 J.

44. The method of claim 27, wherein the initial shock strength is in the range of 10–15 J.

45. The method of claim 44, wherein the initial shock strength is 15 J.

46. The method of claim 27, wherein the implantable cardioverter defibrillator telemeters to a programmer i) a plurality of electrograms, ii) the differentiated electrogram, iii) the base timing point determined in claim 27 (b) (ii), iv) the timing point determined by maximum of the derivative of a T-wave claim 27 (b) (iv), and v) the base time interval in claim 27 (b) (v), (b) the programmer displays on a computer screen a plurality of one or more surface ECG leads and one or more signals taken from electrograms, differentiated electrograms, and timing points and timing intervals telemetered from the implantable cardioverter defibrillator (c) an operator views the screen;

(d) if the operator confirms the timing of timing points indicated in (a) (iii) and (a) (iv) of the present claim using a programmer-input device, the implantable cardioverter defibrillator delivers the test shock in claim 27 (b) (vi);

(e) if the operator does not confirm the timing of timing points indicated in (a) (iii) and (a) (iv) of the present claim, the operator adjusts the timing of one of these points on the programmer, (f) the programmer transmits the adjusted values of these timing points via telemetry to the implantable cardioverter defibrillator, (g) the implantable cardioverter defibrillator uses these adjusted timing points to calculate adjusted base time interval and test-shock time corresponding to the adjusted base time interval plus one of the offset times; and (h) the implantable cardioverter defibrillator delivers the test shock in claim 27 (b) (vi) at the adjusted test-shock time.

47. The method of claim 27, wherein the number of T-wave shocks and their corresponding offset times are functions of the location of the pacing electrode, the syncing electrode, and the shocking electrode.

48. The method of claim 27, wherein the offset times are less than one half the time duration of the T-wave.

49. The method of claim 27, wherein the offset times are less than 100 milliseconds absolute value.

50. The method of claim 49, wherein the offset times are less than 50 milliseconds absolute value.

51. The method of claim 49, wherein the offset times are less than or equal to 40 milliseconds absolute value.

52. The method of claim 49, wherein the offset times are between 0 and 40 milliseconds absolute value.

53. The method of claim 52, wherein at least one offset time is a positive value, to thereby be adapted to deliver a test shock after the maximum of the first derivative of the T-wave with respect to time.

54. The method of claim 52, where in at least one offset time is a negative value, to thereby be adapted to deliver a test shock before the maximum of the first derivative of the T-wave with respect to time.

55. The method of claim 52, wherein one offset time is 0, to thereby be adapted to deliver a test shock substantially at the maximum of the first derivative of the T-wave with respect to time.

56. The method of claim 52, wherein at least one offset time is negative and at least one offset time is positive, to thereby be adapted to deliver at least one test shock after the maximum of the first derivative of the T-wave with respect to time and at least one test shock before the maximum of the first derivative of the T-wave with respect to time.

57. The method of claim 52, wherein a first offset time is 0, a second offset time is −20 milliseconds, a third offset time is −40 milliseconds, and a fourth offset time is +20 milliseconds.

58. The method of claim 52, wherein a first offset time is 0, a second offset time is +20 milliseconds, a third offset time is −20 milliseconds, and a fourth offset time is +40 milliseconds.

59. The method of claim 58, wherein the predetermined waiting period of time is between about 3 minutes and about 5 minutes.

60. The method of claim 52, wherein there are three test shocks with a first offset time of 0, a second offset time of +20 milliseconds a third offset time of −20 milliseconds.

61. The method of claim 27, wherein the offset times in a set are constant.

62. The method of claim 27, wherein the offset times in a set are variable.

63. The method of claim 62, further comprising the step of adjusting the offset times within a set.

64. The method of claim 27, wherein the offset times in each set are identical to offset times in other sets.

65. The method of claim 27, wherein the offset times in at least one set vary relative to offset times in at least one other set.

66. The method of claim 65, further comprising the step of adjusting the offset time of at least one step relative to the offset time of at least one other step.

67. The method of claim 27, wherein the shock strength decrement is in a range of 1–10 J.

68. The method of claim 67, wherein the shock strength decrement is in a range of 2–5 J.

69. The method of claim 68, wherein the shock strength decrement is 5 Joules.

70. The method of claim 27, wherein the shock strength decrement is a constant value.

71. The method of claim 27, wherein the shock strength decrement is a variable value.

72. The method of claim 71, wherein the shock strength decrement is about 5 J for test-shock strengths of greater than or equal to 10 J, and wherein the shock strength decrement is about 2 J for test-shock strengths of less than or equal to 5 J.

73. The method of claim 27, wherein the predetermined sensing time period of step (b) (vii) is 1–10 seconds.

74. The method of claim 27, wherein a waiting period is initiated after the sensing period of step (b)(vii) and prior to repeating sub steps b(i–vii) at the same shock strength.

75. The method of claim 74, wherein the waiting period is about 1 minute.

76. The method of claim 27, initiating a waiting period after the sensing period of sub step (b) (vii) and prior to repeating step (b) at a lower shock strength.

77. The method of claim 76, wherein the waiting period is about 1 minute.

78. The method of claim 27, wherein step (d) further comprises the sub-step of storing the shock value, plus the shock decrement value as the defibrillation threshold energy.

79. The method of claim 27, wherein accomplishing step (b) when the heart is in its native rhythm and choosing the base timing point in relation to timing of the QRS complex.

80. The method of claim 79, wherein the base timing point is the minimum time derivative of the QRS complex.

81. The method of claim 79, wherein the base timing point is the maximum or minimum time derivative with the greatest absolute value of the QRS complex.

82. The method of claim 79, wherein the base timing point is the maximum time derivative of the QRS complex.

83. The method of claim 79, wherein the base timing point is the maximum value of the QRS complex.

84. The method of claim 79, wherein the base timing point is the minimum value of the QRS complex.

85. The method of claim 79, wherein the base timing point is the maximum or minimum of greatest absolute value of the QRS complex.

86. The method of claim 79, accomplishing the step of detecting at least one maximum derivative of a T-wave by selecting a beat in native rhythm.

87. The method of claim 79, accomplishing the step of detecting at least one maximum derivative of a T-wave by calculating an average value from a plurality of native rhythm beats.

88. The method of claim 79, accomplishing the step of detecting at least one maximum derivative of a T-wave by selecting the last beat of a plurality of native rhythm beats in a sequence of native rhythm beats.

89. The method of any of claims 86–88, further comprising the initial step of measuring regularity of native rhythm, and if the rhythm is more irregular than a predetermined threshold value,
   a. waiting a predetermined period of time before implementing step (b);
   b. after step (b) (vi), measuring the regularity of native rhythm; and
   c. if the rhythm is sufficiently regular, delivering any T-wave test shock of step (b) (viii); and
   d. if the rhythm is not sufficiently regular, reinitiating the waiting period.

90. The method of claim 27, further comprising the step before step (b)(i) of pacing the heart and choosing the base timing point in relation to the timing of a pacer spike, and accomplishing step (b) when the heart is in paced rhythm.

91. The method of claim 90, wherein the base timing point is the pacer spike.

92. The method of claim 90, pacing the heart at a cycle length of 500 milliseconds.

93. The method of claim 90, accomplishing the step of detecting at least one maximum derivative of a T-wave by selecting a beat from a plurality of paced beats of a pacing sequence of beats, and utilizing a detected maximum derivative of a T-wave to determine a test-shock time at the end of the pacing sequence.

94. The method of claim 90, accomplishing the step of detecting at least one maximum derivative of a T-wave by calculating an average of a plurality of paced beats of a pacing sequence of beats, and utilizing the detected maximum derivative of a T-wave to determine a test-shock time at the end of the pacing sequence.

95. The method of claim 90, accomplishing the step of detecting at least one maximum derivative of a T-wave by selecting the next-to-last paced beat of a plurality of paced beats in a pacing sequence of beats, and utilizing the detected maximum derivative of a T-wave to determine a test-shock time at the end of the pacing sequence.

96. The method of claim 90, accomplishing the step of detecting at least one maximum derivative of a T-wave is accomplished by selecting a beat from a plurality of paced beats of a pacing sequence of beats, and a detected maximum derivative of a T-wave is utilized to determine a test-shock time at the end of the next pacing sequence.

97. The method of claim 90, accomplishing the step of detecting at least one maximum derivative of a T-wave by calculating an average of a plurality of paced beats of a pacing sequence of beats, and utilizing the detected maximum derivative of a T-wave to determine a test-shock time at the end of the next pacing sequence.

98. The method of claim 90, accomplishing the step of detecting at least one maximum derivative of a T-wave by selecting the next-to-last paced beat of a plurality of paced beats in a pacing sequence of beats, and utilizing the detected maximum derivative of a T-wave to determine a test-shock time at the end of the next pacing sequence.

99. The method of claim 27, performing steps (b–f) within the implantable cardioverter defibrillator device.

100. The method of claim 27, acquiring electrograms from implanted electrodes which are connected to the implantable cardioverter defibrillator and transmitting them electronically from the implantable cardioverter defibrillator device to an external programmer, performing steps (b) (ii)–(v) in the programmer, transmitting test-shock times from the programmer to the implantable cardioverter defibrillator and delivering test shocks by the implanted shock electrodes which are connected to the implantable cardioverter defibrillator.

101. The method of claim 27 wherein
(a) acquiring electrograms from implanted electrodes which are connected to the implantable cardioverter defibrillator and transmitting them electronically from the implantable cardioverter defibrillator to an external programmer,
(b) performing steps (a) and (b) (ii)–(v) in the programmer,
(c) displaying on a computer screen on the programmer one or more signals taken from a plurality of
    i) one or more surface ECG leads;
    ii) a plurality of telemetered electrograms from the implantable cardioverter defibrillator;
    iii) the differentiated electrogram;
    iv) the base timing point determined in claim 30 (b) (ii);
    v) the timing point determined by maximum of the derivative of a T wave in claim 30 (b) (iv); and
    vi) the base time interval in claim 27 (b) (v),
(d) an operator views the screen; and
(e) if the operator confirms the timing of timing points indicated in (c) (iv) and (c) (v) of the present claim transmitting the test shock times from the programmer to the implantable cardioverter defibrillator, which delivers test shocks via the implanted shock electrodes; and
(f) if the operator does not confirm the timing of timing points indicated in (a) (iii) and (a) (iv) of the present claim, the operator adjusts the timing of one of these points resulting in an adjusted base time interval; causing
(g) the programmer to make adjustments in the base time interval and test-shock time corresponding to the base time interval plus one of the offset times; and
(h) transmitting the adjusted test-shock time from the programmer to the implantable cardioverter defibrillator, and
(i) delivering the test shocks from the implantable cardioverter defibrillator to the implanted shock electrodes which are connected to the heart.

102. The method of claim 37, acquiring electrograms from electrodes that are implanted in the patient and connecting them directly to an external implant-support device,
(a) the implant-support device performs steps (a) and (b) (ii)–(v),
(b) a computer screen on the implant-support device displays one or more signals taken from:
    i) one or more surface ECG leads;
    ii) a plurality of electrograms transmitted from implanted electrodes;
    iii) the differentiated electrogram;
    iv) the base timing point determined in claim 27 (b) (ii);
    v) the timing point determined by maximum of the derivative of a T wave in claim 27, (b) (iv); and
    vi) the base time interval in claim 27 (b) (v);
(c) an operator views the screen; and
(d) if the operator confirms the timing of timing points indicated in (a) (iii) and (a) (iv) of the present claim, delivering the test shock from the external implant-support device to the implanted shock electrodes which are connected to the heart; and
(e) if the operator does not confirm the timing of timing points indicated in (a) (iii) and (a) (iv) of the present claim, the operator adjusts the timing of one of these points resulting in an adjusted base time interval, causing
(f) the implant support device to make an adjustment in the test-shock time corresponding to the base time interval plus one of the offset times; and
(g) delivering test shocks by the implant-support device to implanted shock electrodes which are connected to the heart.

103. The method of claim 27, acquiring electrograms from electrodes that are implanted in the patient and connecting them directly to an external implant-support device, performing steps (a–d) in the external implant-support device and delivering test shocks from the external implant-support device to the implanted shock electrodes which are connected to the heart.

104. The method of claim 27, implementing the sensing steps with a plurality of electrodes, and delivering a test shock in step (b)(vi) at a test-shock time relating to the latest-peaking monophasic T-wave detected from any electrode.

105. The method of claim 27, implementing the sensing steps with a plurality of electrodes, and detecting the maximum of the first derivative of the T-wave with respect to time from the electrode in which the derivative of the T-wave reaches its maximum value at the latest time.

106. The method of claim 27, wherein at least one sensing electrode is implanted in a patient and using the at least one implanted sensing electrode to sense electrical activity of the heart.

107. The method of claim 27, wherein the implantable cardioverter defibrillator is electrically connected to a predetermined arrangement of implanted electrodes and communicates with a programmer via a means selected from the group consisting of radio frequency and telemetry.

108. The method of claim 107, wherein the implanted electrodes comprise at least two defibrillation electrodes, at least one of which is intravenously implanted within the heart, at least one implanted sensing electrode, and at least one implanted pacing electrode.

109. The method of claim 27, wherein, if the timing of the maximum of the first derivative of the T-wave with respect to time cannot be reliably detected, comprising the additional steps of:

a. waiting a predetermined period of time; and b. repeating the detecting step (b).

110. The method of claim 27, determining a value of the timing of the maximum derivative T-wave as the average value of a predefined number of beats, and comparing it to a value of the timing of the maximum of the first derivative of the T-wave with respect to time measured on the beat prior to delivery of the test shock, and aborting the test shock if the difference between these two values exceeds a predetermined amount.

111. The method of claim 110, wherein the predetermined amount is 10–100 milliseconds.

112. The method of claim 111, wherein the predetermined amount is 20 milliseconds.

* * * * *